US005670634A

United States Patent [19]
Marotta et al.

[11] Patent Number: 5,670,634
[45] Date of Patent: Sep. 23, 1997

[54] REVERSAL OF β/A4 AMYLOID PEPTIDE INDUCED MORPHOLOGICAL CHANGES IN NEURONAL CELLS BY ANTISENSE OLIGONUCLEOTIDES

[75] Inventors: Charles A. Marotta, Cambridge; Ronald E. Majocha, Needham; Sudhir Agrawal, Shrewsbury, all of Mass.

[73] Assignee: The General Hospital Corporation, Boston, Mass.

[21] Appl. No.: 456,420

[22] Filed: Jun. 1, 1995

Related U.S. Application Data

[63] Continuation of Ser. No. 128,035, Sep. 28, 1993, abandoned.
[51] Int. Cl.$^6$ .............................. C07H 21/00; C12N 15/11
[52] U.S. Cl. .......................................... 536/23.1; 536/23.5
[58] Field of Search ................................ 435/6; 536/23.1, 536/24.3, 24.31, 24.33

[56] References Cited

U.S. PATENT DOCUMENTS

| | | | |
|---|---|---|---|
| 5,149,798 | 9/1992 | Agrawal et al. | 536/25.3 |
| 5,151,510 | 9/1992 | Stec et al. | 536/25.3 |
| 5,242,932 | 9/1993 | Gandy et al. | 514/313 |
| 5,245,022 | 9/1993 | Weis et al. | 536/24.5 |
| 5,316,930 | 5/1994 | Loesch-Fries et al. | 435/172.3 |

FOREIGN PATENT DOCUMENTS

| | | |
|---|---|---|
| WO93/06693 | 7/1989 | WIPO . |
| WO91/06626 | 5/1991 | WIPO . |
| WO91/12323 | 8/1991 | WIPO . |
| WO92/08791 | 5/1992 | WIPO . |
| WO92/10590 | 6/1992 | WIPO . |
| WO92/11390 | 7/1992 | WIPO . |
| WO93/03743 | 3/1993 | WIPO . |
| WO93/13114 | 7/1993 | WIPO . |
| WO95/09236 | 4/1995 | WIPO . |

OTHER PUBLICATIONS

Camarata, P.L., et al., "Sustained release of nerve growth factor from biodegradable polymer microspheres," *Neurosurgery* 30:313–319 (1992).

Ernfors, P. et al., "A cell line producing recombinant nerve growth factor evokes growth respon ses in intrinsic and grafted central cholinergic neurons", *Proc. Natl. Acad. Sci. USA* 86(12):4756–4760 (1989).

Friden, P. et al., "Blood–Brain Barrier Penetration and In–Vivo Activity of an NGF Conjugate," *Science* 30(3):313–319 (1992).

LeBlanc, A. et al., "Role of amyloid precursor protein (APP): study with antisense transfection of human neuroblastoma cells", *J. Neuroscience Research* 31(4):635–645 Apr. (1992).

Marotta, C. et al., "Overexpression of amyloid precursor protein A4 β–amyloid immunoreactivity in genetically transformed cells: implications for a cellular model of Alzheimer amyloidosis", *Proc. Natl. Acad. Sci. USA* 86:337–341 Jan. (1989).

Milward, E. et al., "The amyloid protein precursor of Alzheimer's disease is a mediator of the effects of nerve growth factor on neurite outgrowth", *Neuron* 9(1):129–137 Jul. (1992).

Olson, L., "NGF and the treatment of Alzheimer's disease", *Experimental Neurology* 124:5–15 Nov. (1993).

Refolo, L. et al. "Nerve and epidermal growth factor induce the release of the Alzheimer amyloid precursor from PC12 cell cultures", *Biochemical and Biophysical Research Communications* 164(2): 664–670 Oct. (1989).

Shaw J–P et al., "Modified deoxyoligonucleotides stable to exonuclease degradation of serum", *Nucleic Acid Research* 19(4):747–750 (1991).

Tang J. et al., "Self–stabilized antisense oligodeoxynucleotide phosphorothioates: properties and anti–HIV activity", *Nucleic Acid Research* 21:2729–2735 Jun. (1993).

Kennell, Progr. Nucl. Acidx Res. Mol. Biol. 11; 259–262 (1971).

Syrjanen et al, Neuroscience Letters 130:89 (1991).

Suggs et al, Proc. Natl. Acad. Sci. USA 78:6613 (1981).

Marcus–Sekura, Anal. Biochem. 172:289 (1988).

Eguchi et al, Annu. Rev. Biochem. 60: 631 (1991).

Agrawal & Goodchild, "Oligodeoxynucleoside Methylphosphonates: Synthesis and Enzymic Degradation", *Tetrahedron Lett.* 28:3539–3542 (1987).

Beyreuther et al., "Amyloid precursor protein (APP) and beta A4 amyloid in Alzheimer's disease and Down syndrome", *Prog. Clin Biol. Res.* 379:159–182 (1992).

Cole et al., "The distribution of amyloid plaques in the cerebellum and brain stem in Down's syndrome and Alzheimer's disease: a light microscopical analysis", *Acta Neuropathol* 85:542–552 (1993).

Glenner & Wong, "Alzheimer's disease: intial report of the purification and characterization of a novel cerebrovascular amyloid protein", *Biochem. Biophys. Res. Commun.* 120:885–890 (May 16, 1984).

Glenner & Wong, "Alzheimer's disease and Down's syndrome: sharing of a unique cerebrovascular amyloid fibril protein", *Biochem. Biophys. Res. Commun.* 122:1131–1135 (Aug. 16, 1984).

(List continued on next page.)

*Primary Examiner*—James Martinell
*Attorney, Agent, or Firm*—Hale and Dorr

[57] ABSTRACT

The invention provides oligonucleotides that inhibit the expression of β/A4 peptide of Alzheimer's disease and Down's syndrome, and further provides methods for reversing morphological changes caused in neuronal cells by β/A4 peptide.

10 Claims, 15 Drawing Sheets

OTHER PUBLICATIONS

Ikeda et al., "Evidence of amyloid beta–protein immunoreactive early plaque lesions in Down's syndrome brains", *Lab Invest.* 61:133–137 (1989).

Ikeda et al., "A study of the morphology and distribution of amyloid beta protein immunoreactive plaque and related lesions in the brains of Alzheimer's disease and adult Down's syndrome" *Prog. Clin. Biol. Res.* 317:313–323 (1989).

Kang et al., "The precursor of Alzheimer's disease Amyloid A4 protein resembles a cell–surface receptor" *Nature* 325:733–736 (Feb. 19, 1987).

Maestre et al , "Cell surface extensions associated with overexpression of Alzheimer beta/A4 amyloid", *Brain Res.* 599:64–72 (1992).

Majocha et al. "PC12 cells release stimulatory factors after transfection with beta/A4–C–terminal DNA of the Alzheimer amyloid precursor Protein", *Mol. Chem. Neuropathol.* 18:99–113 (1993).

Majocha et al., "Laminar–specific distribution and infrastructural detail of amyloid in the Alzheimer disease cortex visualized by computer–enhanced imaging of epitopes recognized by monoclonal antibodies", *Proc. Natl. Acad. Sci. USA* 85(16):6182–6186 (Aug. 1988).

Marotta et al., "Overexpression of amyloid precursor protein A4 (beta–amyloid) immunoreactivity in genetically transformed cells: implications for a cellular model of Alzheimer amyloidosis", *Proc. Natl. Acad. Sci. USA* 86:337–341 (Jan. 1989).

Marshall & Caruthers, "Phosphorodithioate DNA as a Potential Therapeutic Drug", *Science* 259:1564–1570 (Mar. 12, 1993)

Masters et al., "Amyloid plaque core protein in Alzheimer disease and Down syndrome", *Proc. Natl. Acad. Sci. USA* 82:4245–4249 (Jun. 1985)

Padmapriya & Agrawal, "Synthesis of Oligodeoxynucleoside Methylphosphonothioates", *Bioorganic & Medicinal Chemistry Letters* 3:761–764 (1993).

Patterson et al., "Mapping of the gene encoding the beta–amyloid precursor protein and its relationship to the Down syndrome region of chromosome 21", *Proc. Natl. Acad. Sci. USA* 85(21):8266–8270 (Nov. 1988).

Schneider & Benner, "Building Blocks for Oligonucleotide analogs with dimethylene–sulfide,–sulfoxide, and –sulfone groups replacing phosphodiester linkages", *Tetrahedron Lett.* 31:335–338 (1990).

Tate et al., "Disruption of circadian regulation by brain grafts that overexpress Alzheimer beta/A4 amyloid", *Proc. Natl. Acad. Sci.* 89(15):7090–7094 (Aug. 1992).

Uhlmann & Peyman, "Antisense Oligonucleotides: A New Therapeutic Principle", *Chemical Reviews* 90:543–584 (Jun. 1990).

| | |
|---|---|
| AGTTTCCTCG GCAGCGGTAG GCGAGAGCAC GCGGAGGAGC GTGCGCGGGG CCCCGGGAGA | 60 |
| CGGCGGCGGT GGCGGCGCGG GCAGAGCAAG GACGCGGCGG ATCCCACTCG CACAGCAGCG | 120 |
| CACTCGGTGC CCCGCGCAGG GTCGCGATGC TGCCCGGTTT GGCACTGCTC CTGCTGGCCG | 180 |
| CCTGGACGGC TCGGGCGCTG GAGGTACCCA CTGATGGTAA TGCTGGCCTG CTGGCTGAAC | 240 |
| CCCAGATTGC CATGTTCTGT GGCAGACTGA ACATGCACAT GAATGTCCAG AATGGGAAGT | 300 |
| GGGATTCAGA TCCATCAGGG ACCAAAACCT GCATTGATAC CAAGGAAGGC ATCCTGCAGT | 360 |
| ATTGCCAAGA AGTCTACCCT GAACTGCAGA TCACCAATGT GGTAGAAGCC AACCAACCAG | 420 |
| TGACCATCCA GAACTGGTGC AAGCGGGGCC GCAAGCAGTG CAAGACCCAT CCCCACTTTG | 480 |
| TGATTCCCTA CCGCTGCTTA GTTGGTGAGT TTGTAAGTGA TGCCCTTCTC GTTCCTGACA | 540 |
| AGTGCAAATT CTTACACCAG GAGAGGATGG ATGTTTGCGA AACTCATCTT CACTGGCACA | 600 |
| CCGTCGCCAA AGAGACATGC AGTGAGAAGA GTACCAACTT GCATGACTAC GGCATGTTGC | 660 |
| TGCCCTGCGG AATTGACAAG TTCCGAGGGG TAGAGTTTGT GTGTTGCCCA CTGGCTGAAG | 720 |
| AAAGTGACAA TGTGGATTCT GCTGATGCGG AGGAGGATGA CTCGGATGTC TGGTGGGGCG | 780 |
| GAGCAGACAC AGACTATGCA GATGGGAGTG AAGACAAAGT AGTAGAAGTA GCAGAGGAGG | 840 |
| AAGAAGTGGC TGAGGTGGAA GAAGAAGAAG CCGATGATGA CGAGGACGAT GAGGATGGTG | 900 |
| ATGAGGTAGA GGAAGAGGCT GAGGAACCCT ACGAAGAAGC CACAGAGAGA ACCACCAGCA | 960 |
| TTGCCACCAC CACCACCACC ACCACAGAGT CTGTGGAAGA GGTGGTTCGA GTTCCTACAA | 1020 |
| CAGCAGCCAG TACCCCTGAT GCCGTTGACA AGTATCTCGA GACACCTGGG GATGAGAATG | 1080 |
| AACATGCCCA TTTCCAGAAA GCCAAAGAGA GGCTTGAGGC CAAGCACCGA GAGAGAATGT | 1140 |

FIG.13A

```
CCCAGGTCAT GAGAGAATGG GAAGAGGCAG AACGTCAAGC AAAGAACTTG CCTAAAGCTG    1200

ATAAGAAGGC AGTTATCCAG CATTTCCAGG AGAAAGTGGA ATCTTTGGAA CAGGAAGCAG    1260

CCAACGAGAG ACAGCAGCTG GTGGAGACAC ACATGGCCAG AGTGGAAGCC ATGCTCAATG    1320

ACCGCCGCCG CCTGGCCCTG GAGAACTACA TCACCGCTCT GCAGGCTGTT CCTCCTCGGC    1380

CTCGTCACGT GTTCAATATG CTAAAGAAGT ATGTCCGCGC AGAACAGAAG GACAGACAGC    1440

ACACCCTAAA GCATTTCGAG CATGTGCGCA TGGTGGATCC CAAGAAAGCC GCTCAGATCC    1500

GGTCCCAGGT TATGACACAC CTCCGTGTGA TTTATGAGCG CATGAATCAG TCTCTCTCCC    1560

TGCTCTACAA CGTGCCTGCA GTGGCCGAGG AGATTCAGGA TGAAGTTGAT GAGCTGCTTC    1620

AGAAAGAGCA AAACTATTCA GATGACGTCT TGGCCAACAT GATTAGTGAA CCAAGGATCA    1680

GTTACGGAAA CGATGCTCTC ATGCCATCTT TGACCGAAAC GAAAACCACC GTGGAGCTCC    1740

TTCCCGTGAA TGGAGAGTTC AGCCTGGACG ATCTCCAGCC GTGGCATTCT TTTGGGGCTG    1800

ACTCTGTGCC AGCCAACACA GAAAACGAAG TTGAGCCTGT TGATGCCCGC CCTGCTGCCG    1860

ACCGAGGACT GACCACTCGA CCAGGTTCTG GGTTGACAAA TATCAAGACG GAGGAGATCT    1920

CTGAAGTGAA GATGGATGCA GAATTCCGAC ATGACTCAGG ATATGAAGTT CATCATCAAA    1980

AATTGGTGTT CTTTGCAGAA GATGTGGGTT CAAACAAAGG TGCAATCATT GGACTCATGG    2040

TGGGCGGTGT TGTCATAGCG ACAGTGATCG TCATCACCTT GGTGATGCTG AAGAAGAAAC    2100

AGTACACATC CATTCATCAT GGTGTGGTGG AGGTTGACGC CGCTGTCACC CCAGAGGAGC    2160

GCCACCTGTC CAAGATGCAG CAGAACGGCT ACGAAAATCC AACCTACAAG TTCTTTGAGC    2220

AGATGCAGAA CTAGACCCCC GCCACAGCAG CCTCTGAAGT TGGACAGCAA AACCATTGCT    2280

TCACTACCCA TCGGTGTCCA TTTATAGAAT AATGTGGGAA GAAACAAACC CGTTTTATGA    2340

TTTACTCATT ATCGCCTTTT GACAGCTGTG CTGTAACACA GTAGATGCC TGAACTTGAA    2400
```

FIG.13B

```
TTAATCCACA CATCAGTAAT GTATTCTATC TCTCTTTACA TTTTGGTCTC TATACTACAT    2460

TATTAATGGG TTTTGTGTAC TGTAAAGAAT TTAGCTGTAT CAAACTAGTG CATGAATAGA    2520

TTCTCTCCTG ATTATTTATC ACATAGCCCC TTAGCCAGTT GTATATTATT CTTGTGGTTT    2580

GTGACCCAAT TAAGTCCTAC TTTACATATG CTTTAAGAAT CGATGGGGGA TGCTTCATGT    2640

GAACGTGGGA GTTCAGCTGC TTCTCTTGCC TAAGTATTCC TTTCCTGATC ACTATGCATT    2700

TTAAAGTTAA ACATTTTTAA GTATTTCAGA TGCTTTAGAG AGATTTTTTT TCCATGACTG    2760

CATTTTACTG TACAGATTGC TGCTTCTGCT ATATTTGTGA TATAGGAATT AAGAGGATAC    2820

ACACGTTTGT TTCTTCGTGC CTGTTTTATG TGCACACATT AGGCATTGAG ACTTCAAGCT    2880

TTTCTTTTTT TGTCCACGTA TCTTTGGGTC TTTGATAAAG AAAAGAATCC CTGTTCATTG    2940

TAAGCACTTT TACGGGGCGG GTGGGGAGGG GTGCTCTGCT GGTCTTCAAT TACCAAGAAT    3000

TCTCCAAAAC AATTTTCTGC AGGATGATTG TACAGAATCA TTGCTTATGA CATGATCGCT    3060

TTCTACACTG TATTACATAA ATAAATTAAA TAAAATAACC CCGGGCAAGA CTTTTCTTTG    3120

AAGGATGACT ACAGACATTA AATAATCGAA GTAATTTTGG GTGGGGAGAA GAGGCAGATT    3180

CAATTTTCTT TAACCAGTCT GAAGTTTCAT TTATGATACA AAAGAAGATG AAAATGGAAG    3240

TGGCAATATA AGGGGATGAG GAAGGCATGC CTGGACAAAC CCTTCTTTTA AGATGTGTCT    3300

TCAATTTGTA TAAAATGGTG TTTTCATGTA AATAAATACA TTCTTGGAGG AGC    3353
```

FIG.13C

REVERSAL OF β/A4 AMYLOID PEPTIDE INDUCED MORPHOLOGICAL CHANGES IN NEURONAL CELLS BY ANTISENSE OLIGONUCLEOTIDES

This application is a continuation of application Ser. No. 08/128,035, filed Sep. 28, 1993, now abandoned.

BACKGROUND OF THE INVENTION

1. Field of the Invention

The invention relates to the treatment of Alzheimer's Disease and Down's syndrome. More particularly, the invention relates to the development of therapeutic agents that are capable of reversing deleterious effects caused by A4 amyloid peptide that are associated with Alzheimer's Disease and Down's syndrome.

2. Summary of the Related Art

Alzheimer's Disease (AD) presents a public health concern of ever increasing importance. Katzman, N. Engl. J. Med. 314:964–973 (1986) teaches that the syndrome is characterized by intellectual deterioration in an adult that is severe enough to interfere with occupational or social performance. Hay and Ernst, Am. J. Pub. Health 77:1169–1175 (1987) teach that AD is the most common form of adult-onset dementia and the fourth leading cause of death in the United States.

The dementia associated with AD correlates with neuropathological changes that are found in the brain. Hyman et al., Science 225:1168–1170 (1984) discloses that the major input and output pathways of the hippocampus have strikingly high concentrations of senile plaques (SPs) and neurofibrillary tangles (NFTs), which may functionally isolate the hippocampus, thereby impairing memory. Mountjoy et al., Aging 4:1–11 (1983) discloses substantial loss of neurons in AD brain. Coyle et al., Science 219:1184–1190 (1983) teach that AD brain shows a decrease in acetylcholine positive sites.

One characteristic commonly associated with AD is the presence of amyloid-containing senile plaques (SPs) in the brain. Majocha et al., Proc. Natl. Acad. Sci. USA 85:6182–6186 (1988) teaches that these plaques range from about 9 to 50 μm in diameter and vary in morphology and density. Wisniewski and Terry, Progress in Neuropathology (Zimmerman, ed.), Grune and Stratton, New York, N.Y., pp. 1–26 (1973) teaches that SPs are composed of extracellular amyloid, reactive cells, degenerating neurites that contain NFTs, lysosomes, abnormal mitochondria and astrocytic processes. Mertz et al., Acta Neuropathol. 60:113–124 (1983) discloses that the core of SPs is formed by amyloid that is composed of fibrils of 4–8 nm in diameter.

The nature of the amyloid from SPs has been determined. Glenner and Wong, Biochem. Biophys. Res. Commun. 120:885–890 (1984) discloses a 4.2 kilodalton AD brain-derived peptide having a unique sequence of 28 amino acids. A polypeptide of similar sequence was also isolated by Glenner and Wong, Biochem. Biophys. Res. Commun. 122:1131–1135 (1984), from the cerebrovascular amyloid of a Down's syndrome brain. A single amino acid substitution, of glutamic acid for glutamine at position 11, distinguished the two proteins. Masters et al., Proc. Natl. Acad. Sci. USA 82:4245–4249 (1985) discloses an amyloid plaque core-derived peptide of 4.2 kd having a nearly identical sequence as the AD-derived peptide of Glenner and Wong, which was relatively insoluble in a variety of solvents. Castano et al., Biochem. Biophys. Res. Commun. 141:782–789 (1986) teaches that short synthetic peptides having structures homologous to the 4.2 kd AD-peptides exhibit similar aggregation properties. Kang et al., Nature 325:733–736 (1987) teaches that the peptide that contributes to senile plaques is a 42 or 43 amino acid stretch cleaved from a larger protein, now known as amyloid precursor protein or APP. The peptide will be referred to herein as β/A4 peptide.

Kang et al., Nature 325:733–736 (1987) proposes that the β/A4 peptide is predominantly comprised of a part of the transmembrane domain of the APP.

Recently, there has been considerable interest in using the tools of molecular biology in determining what role β/A4 peptide might play in the pathology of Alzheimer's disease. Maestre et al., Brain Res. 599:64–72 (1992) teaches that transfected PC12 cells that produce β/A4 peptide are larger than untransfected controls, have longer neurites, and have substantially larger numbers of membrane-limited surface extensions that resemble blebs and microvilli. β/A4 peptide was found to be localized in these membranous processes. Majocha et al., Mol. Chem. Neuropathol. 18:99–113 (1993) teaches that transfected PC12 cells that express β/A4 peptide secrete factors that stimulate neurite lengthening and cell differentiation to a neuronal phenotype. Tate et al., Proc. Natl. Acad. Sci. USA 89:7090–7094 (1992) teaches that transfected cells that express β/A4 peptide can significantly alter circadian activity when grafted into the brain of rats.

Individuals afflicted with Down's syndrome (DS) have brain pathology that is virtually identical to the changes seen in AD. Both NFTs and SPs that are characteristic of AD are seen in DS cases over the age of 40 years. The NFTs and SPs appear to be morphologically and immunohistochemically indistinguishable between the two disorders. Neurochemical alterations are also analogous. See, Ikeda, S. et al., Lab. Invest. 61:133–137 (1989); Cole et al., Acta Neuropathol 85:542–552 (1993); Patterson et al., Proc. Natl. Acad. Sci. 85:8266–8270 (1988); Ikeda et al., Prog. Clin. Biol. Res. 317:313–323 (1989); and Beyreuther et al., Prog. Clin. Biol. Res. 379:159–182 (1992).

These important discoveries indicate an active role for β/A4 peptide in AD and DS neuropathology. However, there is a need to determine whether the pathology attributable to β/A4 peptide is reversible. Development of therapeutic compounds, rather than merely prophylactic agents may well depend upon the reversibility of β/A4 peptide-induced pathology, particularly cell size expansion, neurite extension and differentiation of cells into a neuronal phenotype.

BRIEF SUMMARY OF THE INVENTION

The invention relates to the discovery that it is possible to halt and reverse the accumulation of the beta/A4 peptide in cells which overexpress the peptide. Thus, the invention provides a method for reversing the morphological changes brought upon a cell by β/A4 peptide. In a first aspect, the method according to the invention comprises administering to a cell that is morphologically altered by β/A4 peptide a modified oligonucleotide that reduces or eliminates synthesis of the β/A4 peptide. Modified oligonucleotides that are useful in the method according to the invention are primarily those that are more resistant to nucleolytic degradation than conventional oligonucleotide phosphodiesters. These include oligonucleotides having a variety of modified internucleoside linkages, mixed backbones, nuclease resistant 3' cap structures, integrated triplex-forming structures or self-stabilized structures, or any combination of these. Preferably, the oligonucleotides have a nucleotide sequence that is complementary to the nucleotide sequence encoding β/A4 peptide or its precursor protein APP (see, FIG. 13), or to the initiation codon from which β/A4 peptide or APP is translated. Surprisingly, reduction of β/A4 peptide expression is sufficient to reverse the morphological changes induced by β/A4 peptide, without any apparent need to eliminate other effects that might have been initiated by β/A4 peptide, but subsequently maintained by other molecules. Accordingly, it is of interest to examine the effect of reducing β/A4 peptide levels in a mammal, including a human, to determine the effects of reduced β/A4 peptide upon the entire organism. The invention, in a second aspect, provides a method for making such a determination. Initially, these studies will preferably be conducted in a non-human mammal. Such studies involve administering to the animal such modified oligonucleotides as were previously described for reversing morphological changes brought upon cells by β/A4 peptide.

In a third aspect, the invention also relates to methods for treating or preventing Alzheimer's disease in an animal, in particular, a human.

In a fourth aspect, the invention also relates to methods for treating Down's syndrome in an animal, in particular, a human.

In a fifth aspect, the invention provides oligonucleotides that are effective in reducing β/A4 peptide levels in a cell or an animal, and in reversing morphological changes in a cell that were caused by β/A4 peptide. These oligonucleotides have been briefly described in the discussion of the first aspect of the invention.

In a sixth aspect, the invention also relates to pharmaceutical compositions which comprise an effective amount of at least one of the anti-beta/A4 oligonucleotides of the present invention together with a pharmaceutically acceptable carrier.

BRIEF DESCRIPTION OF THE DRAWINGS

FIGS. 13A and 13B depict the cDNA sequence of APP [SEQ ID NO. 12] disclosed by Kang et al., Nature 325:733–736 (1987), from which anti-beta/A4 oligonucleotides can be constructed which are complementary to the corresponding mRNA sequence. The initiation codon begins with nucleotide 147. The coding sequence of the β/A4 protein extends from nucleotide 1935 through 2060. The APP coding sequence ends at nucleotide 2231.

DETAILED DESCRIPTION OF THE PREFERRED EMBODIMENTS

Figure 1:
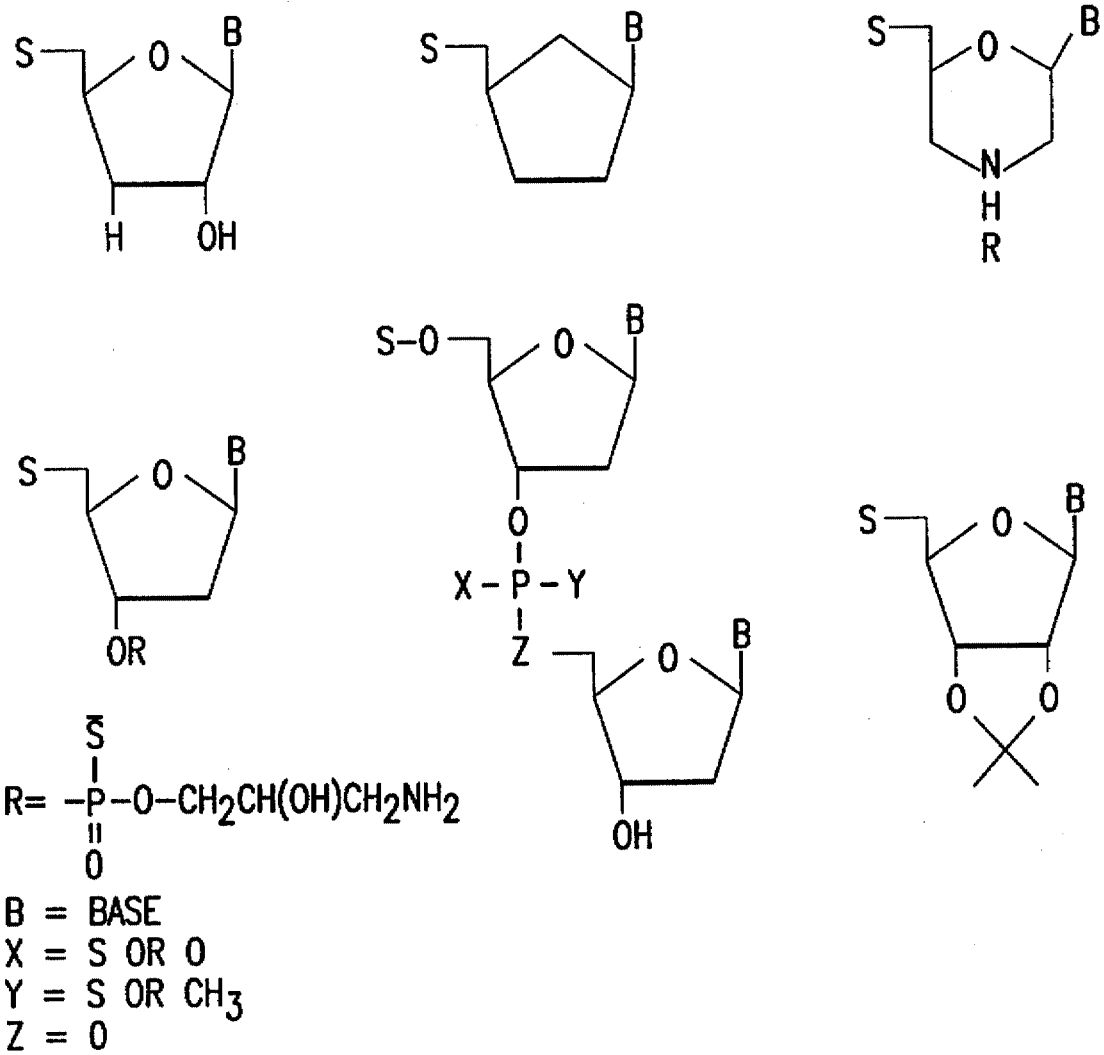
FIG. 1 shows certain preferred cap structures used in one embodiment of oligonucleotides according to the invention.

The invention relates to the development of therapeutic treatments for Alzheimer's disease (AD) and Down's syndrome (DS). The invention provides potential therapeutic agents that are capable of preventing and reversing deleterious effects that are visited upon cells by β/A4 amyloid peptide, a peptide that is important to the pathology of AD and DS.

In a first aspect, the invention provides a method of reversing morphological changes induced upon cells by expression of β/A4 peptide. In this method according to the invention anti-β/A4 oligonucleotides are administered to cells that express β/A4 peptide, and that have undergone morphological changes as a result of their expression of β/A4 peptide. Such morphological changes include, but are not limited to, cell size enlargement, cellular aggregation, formation of bleb and/or microvilli-like membrane processes, and increases in neurite length.

In the method according to the invention, "anti-β/A4 oligonucleotides" are defined as those oligonucleotides that have a nucleotide sequence that interacts through specific Watson-Crick or Hoogstein base pairing with a specific complementary nucleic acid sequence involved in the expression of β/A4 peptide, such that the expression of the β/A4 peptide is reduced. Preferably, the interaction between the oligonucleotide and the specific nucleic acid sequence involved in the expression of the β/A4 peptide is either duplex formation by Watson-Crick base pairing, triplex formation by Hoogstein base pairing, or a combination of these. Preferably, the specific nucleic acid sequence involved in the expression of β/A4 peptide is a gene or RNA molecule that encodes at least β/A4 peptide. In this context, the term "gene" describes a structure comprising a promoter, a nucleotide sequence encoding at least β/A4 peptide, and a passive terminator. In one most preferred embodiment, this gene is the well known APP gene. Similarly, the term "RNA" is intended to encompass nuclear or messenger RNA encoding at least β/A4 peptide. Preferably, such RNA encodes APP protein. In certain embodiments of the method according to the invention, the oligonucleotides administered to cells will be complementary to a nucleotide sequence comprising the initiation codon from which the β/A4 peptide is translated. The term "complementary to a nucleotide sequence" means sufficiently complementary to such a sequence as to allow hybridization to that sequence in a cell, i.e., under physiological conditions. As a practical matter, the presence or absence of such hybridization can be assessed by determining whether gene expression is reduced. The term "initiation codon from which β/A4 peptide is translated" means a translation initiation codon that acts as the beginning codon for translation that produces a polyamino acid product that comprises β/A4 peptide. In a most preferred embodiment, the initiation codon is the initiation codon for APP. In certain other embodiments, the method according to the invention utilizes administration of oligonucleotides that are complementary to nucleotide sequences that encode β/A4 peptide. Alternatively, such oligonucleotides may be complementary to a nucleotide sequence that comprises a nucleotide sequence encoding β/A4 peptide. A preferred example of such latter oligonucleotides is an oligonucleotide that is complementary to a nucleotide sequence that encodes APP. Particular examples of such oligonucleotides include, but are not limited to:

1. [SEQ ID NO. 1] 5'-CCTCTCTGTTTAAAACTTTATCCAT-3';
2. [SEQ ID NO. 2] 5'-TTCATATCCTGAGTCATGTCG-3';
3. [SEQ ID NO. 3] 3'-GTCCCAGCGCTACGACGGGCCAAA-5';
4. [SEQ ID NO. 4] 3'-GTCCCAGCGCTAC-5';
5. [SEQ ID NO. 5] 3'-TACGACGGGCCAAA-5';
6. [SEQ ID NO. 6] 3'-GTCCCAGCGCTACGACGGGCC-5';
7. [SEQ ID NO. 7] 3'-GTCCCAGCGCTACGACGG-5';
8. [SEQ ID NO. 8] 3'-GTCCCAGCGCTACGA-5';
9. [SEQ ID NO. 9] 3'-CCAGCGCTACGACGGGCCAAA-5';
10. [SEQ ID NO. 10] 3'-GCGCTACGACGGGCCAAA-5'; and
11. [SEQ ID NO. 11] 3'-CTACGACGGGCCAAA-5'.

Preferred oligonucleotides that are useful in the method according to this aspect of the invention are discussed in greater detail later in a discussion of a third aspect of the invention. Briefly, they are generally more resistant to nucleolytic degradation than conventional oligonucleotide phosphodiesters. In certain preferred embodiments, such oligonucleotides may have any of a variety of modified internucleoside linkages, mixed backbones, nuclease resistant 3' cap structures, integrated triplex-forming structures, or self-stabilized structures, or any combination of these.

The method according to this aspect of the invention is useful for a variety of purposes. In basic science applications, this method can provide information about the dosage or level of expression of β/A4 peptide that is necessary to produce each of the morphological changes in cells. This can be accomplished by reducing the quantity of oligonucleotide administered to the cells, such that the expression of β/A4 peptide is only partially reduced. The method can also provide information about the time and sequence of morphological changes induced by β/A4 peptide, by first fully reversing the changes, then removing the oligonucleotide and observing the timing and sequence of the recurrence of the changes. In applied science applications, the method provides information about the specific nature of the oligonucleotides that are most effective for reversing the morphological changes induced by β/A4 peptide. The instant disclosure reveals that, surprisingly, oligonucleotides can reverse morphological changes induced by β/A4 peptide. Moreover, however, through examining the dosage requirements and degree of morphology change reversal, the method allows those skilled in the art to determine the most efficacious combination of nucleotide sequence, backbone composition, secondary structure, base modification, etc., for reversal of morphological changes.

In a second aspect, the invention provides a method for reducing β/A4 peptide expression in an animal, including a human. In the method according to this aspect of the invention, oligonucleotides are administered to an animal and cause the reduction in β/A4 peptide expression. For administration to a nonhuman animal, the nucleotide sequence of the oligonucleotides is selected to be complementary to the appropriate nonhuman β/A4 peptide or APP gene. The chemical composition of the oligonucleotides is described in detail in the discussion below of the third aspect of the present invention. These oligonucleotides act in the same manner as described for the method according to the first aspect of the invention. The oligonucleotides may be administered orally, intravenously, intranasally, intraperitoneally, anally, by injection into the cerebrospinal fluid, or by direct injection into the brain. Alternatively, the oligonucleotides of the present invention are compounded as part of an implant comprising a polymeric carrier or capsule which allows for sustained release. Such polymeric carriers are disclosed, for example, in Remington's *Pharmaceutical Sciences*, 18th Ed., Mack Publishing Co., Easton, Pa., Osol (ed.) (1990). In a further embodiment, the oligonucleotides of the present invention may be continuously administered by a pump implant or an external pump.

Preferably, the oligonucleotides are administered at a dosage of from about 1 to about 100 mg/kg of animal body weight.

The anti-beta/A4 oligonucleotides are administered as part of pharmaceutical compositions comprising a pharmaceutically acceptable carrier which may be, for example, physiologic saline or physiologic glucose solution. Aqueous injection suspensions may contain substances which increase the viscosity of the suspension include, for example, sodium carboxymethyl cellulose, sorbitol, and/or dextran. Optionally, the suspension may also contain stabilizers. Methods for preparing and administering such pharmaceutical compositions may be found in Remington's *Pharmaceutical Sciences*, 18th Ed., Mack Publishing Co., Easton, Pa., Osol (ed.) (1990).

In initial studies, the oligonucleotides are preferably administered to a nonhuman animal, most preferably a mammal. Such administration provides information about the most efficacious dosage and route of administration for reducing β/A4 peptide expression in the animal. Subsequently, the oligonucleotides are administered to a human suffering from AD or DS. Such administration is expected to reverse morphological changes induced upon brain cells by the β/A4 peptide, thus bringing about a therapeutic effect.

In a third aspect, the invention provides anti-β/A4 oligonucleotides that are useful for reversing the morphological changes that are induced upon cells by β/A4 peptide. The "anti-β/A4 oligonucleotides" according to the invention encompass those oligonucleotides that have a nucleotide sequence that interacts with a specific nucleic acid sequence involved in the expression of β/A4 peptide, such that the expression of the β/A4 peptide is reduced. Preferably, the interaction between the oligonucleotide and the specific nucleic acid sequence involved in the expression of β/A4 peptide is either duplex formation by Watson-Crick base pairing, triplex formation by Hoogstein base pairing, or a combination of these. See, for example, PCT publication Nos. WO91/06626, WO92/08791, WO92/11390, and WO92/10590. Preferably, the specific nucleic acid sequence involved in the expression of β/A4 peptide is a gene or RNA molecule that encodes at least β/A4 peptide. In this context, the term "gene" describes a structure comprising a promoter, a nucleotide sequence encoding at least β/A4 peptide, and a passive terminator. In one most preferred embodiment, this gene is the well known APP gene. Similarly, the term "RNA" is intended to encompass nuclear or messenger RNA encoding at least β/A4 peptide. Preferably, such RNA encodes APP protein. In certain embodiments of this aspect of the invention, the oligonucleotides are complementary to a nucleotide sequence comprising the initiation codon from which β/A4 peptide is translated. The term "complementary to a nucleotide sequence" means sufficiently complementary to such a sequence as to allow hybridization to that sequence in a cell, i.e., under physiological conditions. As a practical matter, the presence or absence of such hybridization can be assessed by determining whether gene expression is reduced. The term "initiation codon from which β/A4 peptide is translated" means a translation initiation codon that acts as the beginning codon for translation that produces a polyamino acid product that comprises β/A4 peptide. In a most preferred embodiment, the initiation codon is the initiation codon for APP. In certain other embodiments, the anti-β/A4 oligonucleotides are complementary to nucleotide sequences that encode β/A4 peptide. Alternatively, such oligonucleotides may be complementary to a nucleotide sequence that comprises a nucleotide sequence encoding β/A4 peptide. A preferred example of such latter oligonucleotides is an oligonucleotide that is complementary to a nucleotide sequence that encodes APP. Such oligonucleotides may comprise about 8 to about 100 nucleotide bases.

Anti-β/A4 oligonucleotides according to the invention may optionally have additional ribonucleotide, 2'-substituted ribonucleotide, and/or deoxyribonucleotide monomers, any of which are connected together via 5' to 3' linkages which may include any of the internucleotide linkages known in the art. Preferably, such modified oligonucleotides may optionally contain phosphodiester, phosphotriester, phosphoramidate, siloxane, carbonate, carboxymethylester, acetamidate, carbamate, thioether, bridged phosphoramidate, bridged methylene phosphonate, bridged phosphoramidate, bridged methylene phosphonate, bridged phosphorothioate and/or sulfone internucleotide linkages. Those skilled in the art will recognize that the synthesis of oligonucleotides containing any of these internucleotide linkages is well known to those skilled in the art, as is illustrated by articles by Uhlmann and Peyman, *Chemical Reviews* 90:543–584 (1990) and Schneider and Banner, *Tetrahedron Lett.* 31:335 (1990). Preferably, modified oligonucleotides according to the invention should contain from about 6 to about 100 monomers in total. Such modified oligonucleotides may also optionally contain modified nucleic acid bases and/or sugars, as well as added substituents, such as diamines, cholesteryl or other lipophilic groups.

In one preferred embodiment, anti-β/A4 modified oligonucleotides according to the invention are in the form of a mixed backbone oligonucleotide having one or more regions of nucleotides connected by phosphorothioate or phosphorodithioate internucleotide linkages ("phosphorothioate or phosphorodithioate region") as well as one or more regions of nucleotides connected by alkylphosphonate or alkylphosphonothioate internucleotide linkages ("alkylphosphonate or alkylphosphonothioate region"). In this embodiment, at least one alkylphosphonate region preferably includes nucleotides at or near the 5' end and/or the 3' end of the oligonucleotide. For purposes of the invention, "at or near the 5' or the 3' end of the oligonucleotide" means involving at least one nucleotide within about 5 nucleotides from the 5' or 3' end of the oligonucleotide. Preferably, the alkylphosphonate or alkylphosphonothioate region comprises from about 2 to about 10 contiguous nucleotides connected by alkylphosphonate linkages. Preferably, the phosphorothioate or phosphorodithioate region comprises at least 3, and up to about 100 contiguous nucleotides connected by phosphorothioate or phosphorodithioate linkages.

Anti-β/A4 modified oligonucleotides according to this embodiment of the invention are synthesized by solid phase methods, alternating H-phosphonate chemistry and sulfur oxidation for phosphorothioate regions, and alkylphosphonamidate chemistry for alkylphosphonate regions. A preferred H-phosphonate approach is taught by Agrawal et al., U.S. Pat. No. 5,149,798, the teachings of which are hereby incorporated by reference. Alkylphosphonamidite chemistry is well known in the art, as illustrated by Agrawal and Goodchild, *Tetrahedron Lett.* 28:3539–3542 (1987). Synthesis of phosphorodithioate-containing oligonucleotides is also well known in the art, as illustrated by U.S. Pat. No. 5,151,510, the teachings of which are hereby incorporated by reference (See also, e.g., Marshall and Caruthers, *Science* 259:1564–1570 (1993) and references cited therein). Finally, synthesis of alkylphosphonothioate-containing oligonucleotides is known in the art, as illustrated by Padmapriya and Agrawal, *Bioorganic & Medicinal Chemistry Letters* 3:761–764 (1993).

In another preferred embodiment, anti-β/A4 modified oligonucleotides according to the invention are in the form of a hybrid oligonucleotide having regions of deoxyribonucleotides ("deoxyribonucleotide regions") and regions of ribonucleotides or 2'-substituted ribonucleotides ("ribonucleotide regions"). Preferably, from about one to about all of the internucleotide linkages are phosphorothioate or phosphorodithioate linkages. Preferred 2'-substituted ribonucleotides are halo, amino, alkyl, aryl or lower alkyl (1–6 carbon atoms) substituted ribonucleotides, especially 2'-OMe-ribonucleotides. Preferably, at least some of the ribonucleotide regions include nucleotides present at or near the 5' end and/or the 3' end of the oligonucleotide. Most preferably, the ribonucleotide regions each comprise from about 2 and preferably from about 4 to about 100 contiguous ribonucleotides and/or 2'-substitute oligonucleotides. The deoxyribonucleotide regions are optional, and when present may contain from about 1 to about 100 contiguous deoxyribonucleotides.

Anti-β/A4 oligonucleotides according to this embodiment of the invention are typically synthesized by solid phase methods, preferably by the phosphoramidite or H-phosphonate approach, using deoxynucleotide H-phosphonates for deoxyribonucleotide regions, and ribonucleotide or 2'-substituted ribonucleotide H-phosphonates for ribonucleotide regions.

In yet another preferred embodiment, anti-β/A4 oligonucleotides according to the invention are in the form of an oligonucleotide having at its 5' and/or preferably at its 3' end a cap structure that confers exonuclease resistance to the oligonucleotide. Such modified oligonucleotides preferably also have from 1 to about all modified (non-phosphodiester) internucleotide linkage. Preferred cap structures include those shown in FIG. 1, as well as lower alkyl (C1–C12) or alcohol groups. Preferred modified internucleotide linkages include phosphotriester, phosphoramidate, siloxane, carbonate, carboxymethylester, acetamidate, carbamate, thioether, bridged phosphoramidate, bridged methylene phosphonate, bridged phosphorothioate, sulfone, phosphorothioate and phosphorodithioate linkages.

Anti-β/A4 oligonucleotides according to this embodiment of the invention are synthesized according to procedures well known in the art (see e.g., Uhlmann and Peyman, *Chemical Reviews* 90:543–584 (1990); Schneider and Banner, *Tetrahedron Lett.* 31:335 (1990)). For oligonucleotides having cap structures at the 3' end, the cap structure is reversibly attached to the solid support and is then coupled to the first nucleotide monomer in the synthesis scheme. For oligonucleotides having cap structures at the 5' end, the cap structure is coupled to the end of the oligonucleotide after addition of the last nucleotide monomer in the synthesis scheme.

Figure 2:
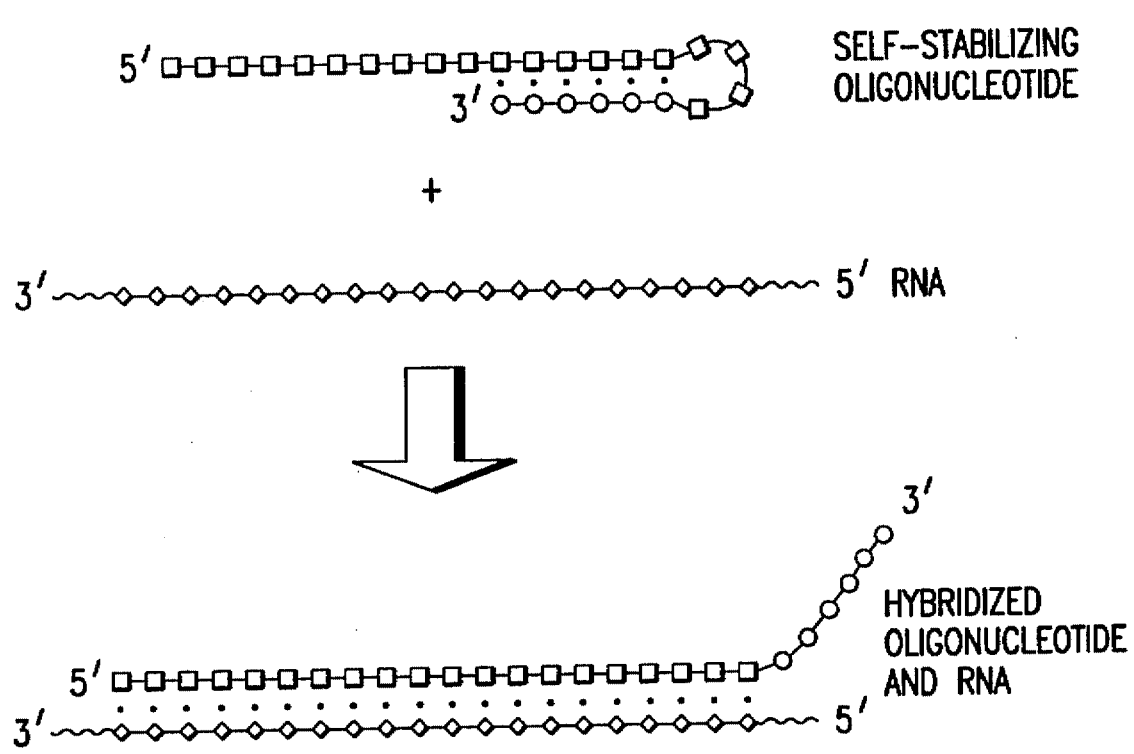
FIG. 2 shows one form of a self-stabilized oligonucleotide embodiment according to the invention.

In another preferred embodiment, anti-β/A4 oligonucleotides are self-stabilized by having a self-complementary region at the 3' end that hybridizes intramolecularly with the oligonucleotide to form an exonuclease resistant hairpin-like structure. Anti-β/A4 oligonucleotides according to this embodiment of the invention are generally characterized by having two regions: a target hybridizing region and a self-complementary region. The target hybridizing region has a nucleotide sequence that is complementary to the targets described earlier. Preferably, this region has from about 6 to about 100 nucleotides. One form of this embodiment of the invention is shown in FIG. 2. In this form, the target hybridizing region is shown as connected rectangular squares, and the self-complementary region is shown as connected circles. The complementary nucleic acid sequence in a target influenza messenger RNA molecule is represented by connected diamonds. Hydrogen bonding between nucleotides is indicated by dots. The oligonucleotide is stabilized, i.e., rendered resistant to exonucleolytic degradation by base-pairing between the target hybridizing region and the self-complementary region and/or by base-pairing between complementary sequences within the self-complementary region. When the oligonucleotide encounters a target nucleic acid molecule having a complementary nucleic acid sequence, base-pairing between the target hybridizing region and the self-complementary region of the oligonucleotide is disrupted and replaced by base-pairing between the target hybridizing region of the oligonucleotide and the complementary nucleic acid sequence of the target nucleic acid molecule. This disruption and replacement of base-pairing takes place because the intermolecular base-paired structure formed by the hybrid between the target nucleic acid sequence and the target hybridizing region is more thermodynamically stable than the intramolecular base-paired structure formed by the self-complementary oligonucleotide.

Figure 3:
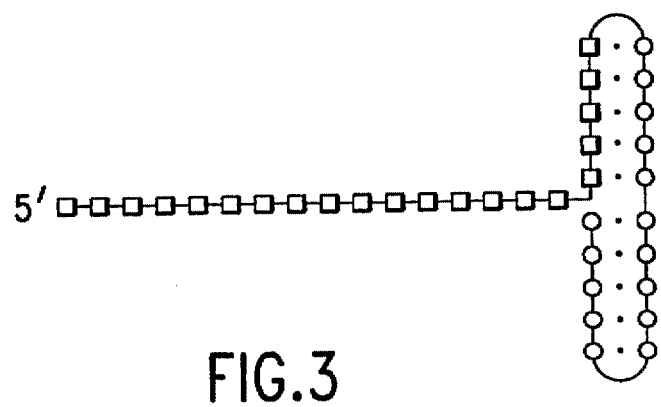
FIG. 3 shows a second form of a self-stabilized oligonucleotide embodiment according to the invention.

A second form of an oligonucleotide according to this embodiment of the invention operates in a similar way as the first form, but forms a different structure upon self-complementary base-pairing. This alternative form forms a hammer-like structure as shown in FIG. 3. In this form, the self-complementary region contains oligonucleotide sequences that can base pair with other oligonucleotide sequences within the self-complementary region. The self-complementary region may also contain oligonucleotide sequences that are complementary to the target hybridizing region.

The second significant region of self-stabilized oligonucleotides according to the invention is the self-complementary region. The self-complementary region contains oligonucleotide sequences that are complementary to other oligonucleotide sequences within the oligonucleotide. These other oligonucleotide sequences may be within the target hybridizing region or within the self-complementary region, or they may span both regions. The complementary sequences form base pairs, resulting in the formation of a hairpin structure, as shown in FIG. 2, or a hammer-like structure, as shown in FIG. 3. Either the hairpin structure or the hammer-like structure can have loops resulting from non-base-paired nucleotides, as shown in FIG. 2 for the hairpin structure, or can be devoid of such loops, as shown in FIG. 3 for the hammer-like structure. The number of base-pairs to be formed by intra-molecular hybridization involving the self-complementary region may vary, but should be adequate to maintain a double-stranded structure so that the 3' end is not accessible to exonucleases. Generally, about 4 or more base-pairs will be necessary to maintain such a double-stranded structure. In a preferred embodiment, there are about 10 intramolecular base-pairs formed in the self-stabilized oligonucleotide, with the 10 base pairs being consecutive and involving the 3'-most nucleotides. Of course, the intra-molecular base-pairing can be so extensive as to involve every nucleotide of the oligonucleotide. Preferably, this will involve a self-complementary region of about 50 nucleotides or less.

Oligonucleotides according to this embodiment may have from 1 to about all modified internucleotide linkages, as described for the fourth embodiment. Preferably, at least either the target hybridizing region or the self-complementary region, and most preferably both, will contain from about 2 to about all nucleotides being coupled by phosphorothioate and/or phosphorodithioate linkages.

Those skilled in the art will recognize that the features of the various preferred embodiments described above can be combined to produce additional embodiments that may have even greater anti-β/A4 effect.

Anti-β/A4 oligonucleotides according to the invention are useful for a variety of purposes. First, they are useful for reversing morphological changes in cells in vitro that are caused by expression of β/A4 peptide. Second, they are useful for examining the effect of reduced β/A4 peptide expression in animals, including humans. Third, they are useful for conducting clinical trials designed to obtain marketing approval for such oligonucleotides as therapeutic agents for Alzheimer's disease. Fourth, they are useful for treating patients suffering from Alzheimer's disease and/or preventing or delaying the onset of the disease. Finally, they are useful for treating patients which are suffering from DS.

The following examples are intended to further illustrate certain preferred embodiments of the invention and are not intended to be limiting in nature. The work described in Examples 1 and 2 below has previously been published in *Proc. Natl. Acad. Sci. USA* 86:337–341 (1989) and *Brain Research* 599:64–72 ( 1992).

EXAMPLE 1

Development of a PC12 Cell Line that Overexpresses β/A4 Peptide

Figure 4:
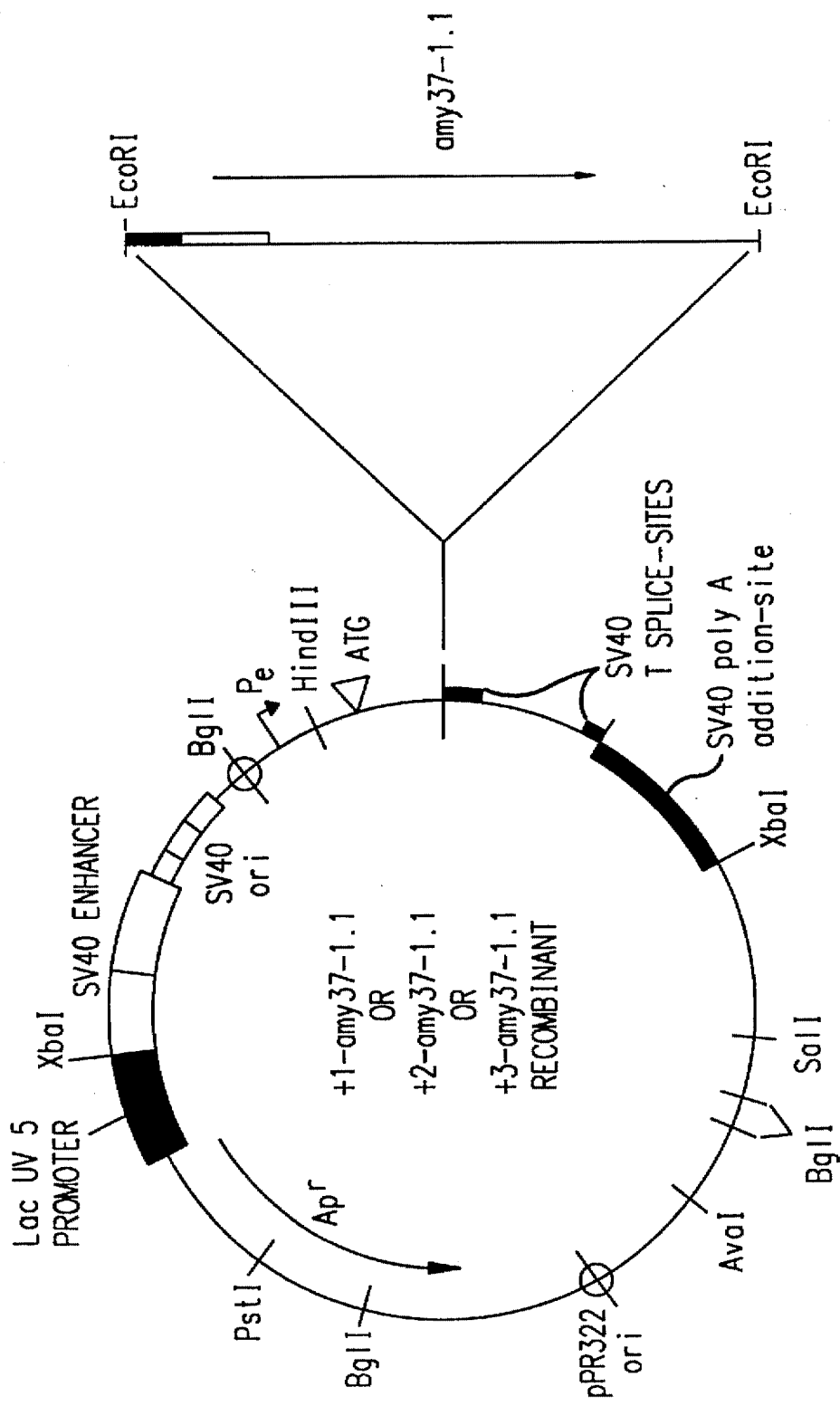
FIG. 4 shows a schematic representation of Min vectors containing amyloid cDNA. The insert segment shown harbors the β/A4 peptide (black vertical box), the rest of the APP coding sequence (open vertical box) and noncoding region (thin vertical line).

The initial cloning vehicle was a simian virus 40(SV40)-based vector pKo+RI/ML, composed of $PML_2$, a derivative of pBR322 (lacking certain prokaryotic sequences poisonous for eukaryotic cell replication), the Lac UV5 promoter of *Escherichia coli*, and SV40 sequences covering the enhancer, origin of replication, early promoter, small tumor (t)/large tumor (T) antigen splice sites, and polyadenylation sites. Modification of the initial vector was carried out to produce three variants, Min+1, Min+2, and Min+3 with three different translational reading frames using the ATG codon of the T/t antigen (see FIG. 4). The starting vector or modified forms were used for experimentation. The precursor to the Min series contained a unique Pvu II site (enhancer start) and a BamHI site [poly(A) addition site], both of which were modified to Xba I sites by standard techniques.

From an AD brain cDNA expression vector library prepared with bacteriophage λ we obtained an insert, referred to as amy37, that included the A4 sequence and the flanking regions. The Min vector constructs were used for insertion of the EcoRI-digested amy37 cDNA fragment in the three transitional reading frames. Vectors were digested with EcoRI restriction endonuclease to cleave at the unique EcoRI site and with alkaline phosphatase. The λt11-amy37 chimera was digested with EcoRI enzyme and the 1.1-kilobase (kb)-long fragment was ligated into the Min vectors by established techniques. The amy37-1.1 chimeric plasmids generated separately in the three reading frames were propagated, then the DNA was isolated, purified and used for transfection experiments. The cell line used for these experiments was PC12, derived from rat adrenal pheochromocytoma.

Conventional permanent transfection experiments were conducted. Integration of the 1.1-kb amyloid cDNA insert was carried out using transfection medium containing 10 μg of vector with amy37-1.1 inserts or a control consisting of vector DNA without an amyloid cDNA insert, 5 μg of $PSV_2CAT$ DNA (the chloramphenicol acetyltransferase gene cloned into an SV40-based plasmid), which carried the gene for neomycin resistance that was sensitive to Geneticin. The various transfectants were selected for survival in the presence of Geneticin (G418, GIBCO) at a concentration of 0.4 g/liter for 6 days and then at 0.3 g/liter for 3 days; the cells were subsequently maintained at 0.2 g/liter. The cells shown in accompanying figures had undergone at least 20 cell divisions.

DNA was isolated from cells, and Southern blots were prepared. Nytran filters were hybridized overnight at 52° C. in hybridization solution containing 3× Denhardt's solution (1× Denhardt's solution=0.02% polyvinylpyrrolidone/ 0.02% Ficoll/0.02% bovine serum albumin) and amy37-1.1 riboprobe at 8 ng/ml ($2.5×10^6$ cpm/ml) that had been denatured by heating at 80° C. for 8 min. The riboprobe prepared had a specific activity of $3.1×10^8$ cpm/μg. The filters were washed twice for 5 min in 2×SSC (1×SSC=0.15M NaCl and 0.015M sodium citrate)/0.1% sodium dodecyl sulfate (SDS) at 25° C. and then twice for 30 min. in 0.1% SSC/0.1% SDS at 53° C. The filters were air dried and used for autoradiography. β/A4 C-terminal transfectants exhibited a hybridization signal corresponding to a human β/A4 DNA fragment of around 1200–1300 b.p., the size of the known EcoRI fragment encoding the C-terminal region.

Figure 5A:
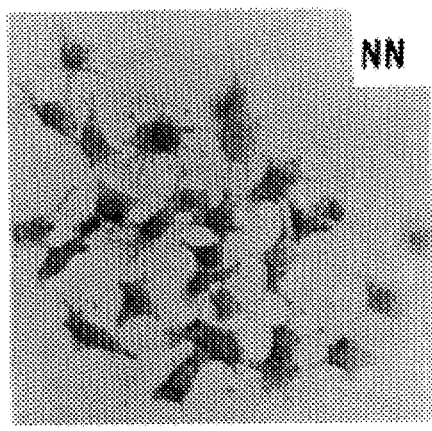
FIG. 5 shows immunostaining patterns for untransfected cells (Panel A), cells containing the transforming vector without an amyloid insert (Panel B) and cells transfected with vector DNA coding for the region from A4 to the C-terminus of APP (Panel C).
Figure 5B:
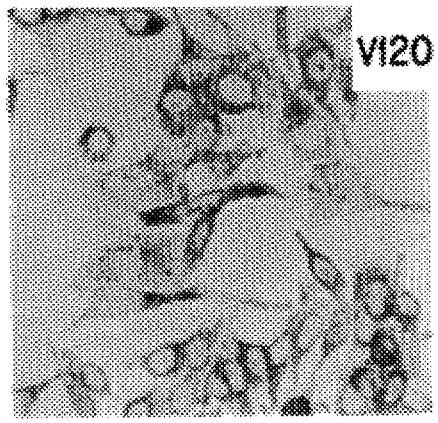
Figure 5C:
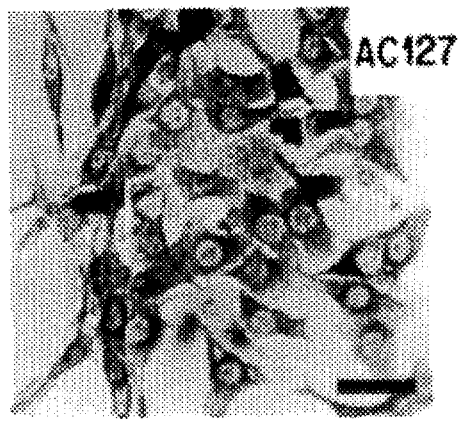
Figure 6A:
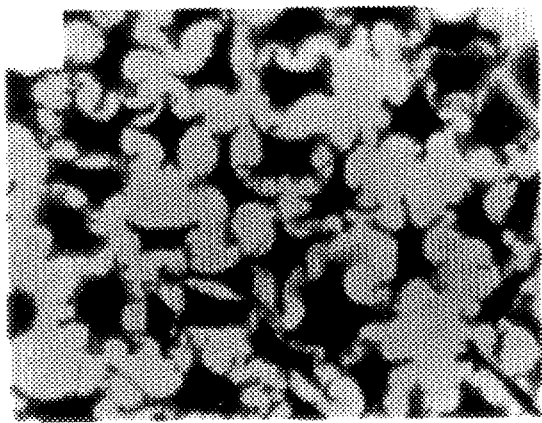
FIG. 6 shows light micrographs of β/A4 transfected AC126 (Panel C) and AC127 (Panel D) cells compared with untransfected cells (Panel A) or cells transfected with insertless vector (Panel B).
Figure 6B:
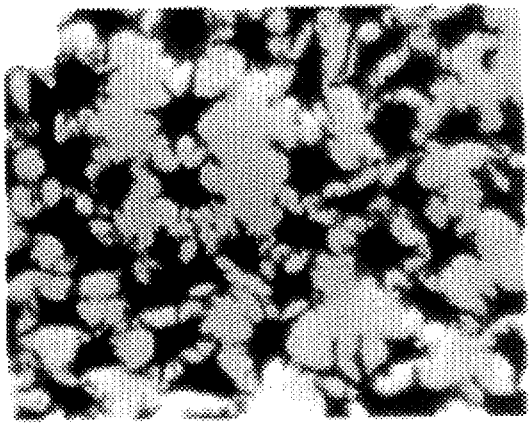
Figure 6C:
Figure 6D:
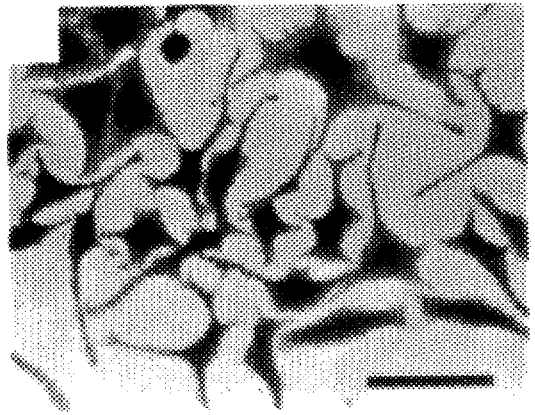

PC12 cells were immunostained before and after transfection with the in-frame vector Min+2amy37-1.1 and the out-of-frame vector Min+3-amy37-1.1. Logarithmic phase cultures of non-transfected cells and those carrying the vector without the A4-coding insert typically exhibited barely detectable antigen levels after application of the anti-A4 mAbs (FIGS. 5A and 5B, respectively). However, the in-frame vector produced cells with unusually high levels of reaction product after immunostaining (FIG. 5C). In some instances the antigen appeared concentrated around the periphery or was localized to one end of the cell. Dividing cells exhibited lighter immunostaining with an uneven distribution of reaction product. PC12 cell lines that overexpress the A4 epitope have been propagated in culture for a period of >2 months. The cell lines examined were designated NN (untransfected PC12 cells), V120 (insertless vector-transfected PC12 cells), AC126 and AC127 (β/A4 C-terminal peptide expressing PC12 cells).

EXAMPLE 2

Assessment of Altered Morphology Cells Overexpressing β/A4 Peptide

Cell size and length of neurites were determined at the light microscope level using an image analysis measurement system containing microdensitometry computer software (Bioquant, R&M Biometrics, Inc., Nashville, Tenn.). Cells were grown for 48 hours on glass chambered slides and were rinsed in Hanks buffered saline before being fixed in 4% paraformaldehyde for 30 min. Following rinsing, cells were stained with Coomassie blue for 5 min. Slides were then rinsed, dried and coverslipped. Fields of cells were examined with a Leitz microscope at 40×. Using the image measurement system, the boundary of the cell body was outlined and the mean area of the cell body was calculated. The neurites from each measured cell were traced and neurite length was calculated. Data was derived from counting 100 V120 cells from two separate experiments and 150 NN, AC126 and AC127 cells from three separate experiments. Data were compared by analysis of variance.

For electron microscopy, cells were fixed with 2% paraformaldehyde, 2.5% glutaraldehyde in 0.1M cacodylate buffer (pH 7.4) for 30 min, postfixed with $OsO_4$ for 30 min, dehydrated through graded ethanols, and embedded in Epon on coverslipped glass slides. Sections were cut using an ultra-microtome (60 nm) and placed on grids. The grids were examined with JEOL 1200EX electron microscope at a magnification of 5,000×, 10,000× and 40,000×. For the purposes of quantitating membranous structures, montages of photographs were made with pictures photographed at 5,000×.

Membrane processes were observed that resembled previously described microvilli and blebs. The former appear in electron micrographs as rounded or finger-like membrane limited cytoplasmic protrusions at the cell surface with a diameter ranging from 0.1 to 10 μm. Other processes appeared similar to blebs since they contained ribosomes or endoplasmic reticulum in the interior. Blebs often appeared as vesicles at the cell surface which is presumed to reflect the section plane of the block.

For immunoelectron microscopy, cells were grown in 35 mm plastic plates. The plates were rinsed briefly with Hank's salt solution and fixed with fresh 4% paraformaldehyde in 0.13M NaCl, 0.02M phosphate buffer, pH 7.4 (PBS) for 30 minutes at room temperature. They were rinsed 3 times with PBS for 10 minutes each time.

Cells were immunostained with monoclonal antibodies (IgG) against a synthetic polypeptide with β/A4 sequence. For comparative studies a second mAb, that lacks affinity for membrane antigens, was used. In this case the mAb was prepared to alkaline ribonuclease inhibitor protein (RIP) (Promega), an intracytoplasmic regulatory protein that functions to stabilize RNA and ribosomes. The supernatant from the hybridoma cell line making anti-RIP antibodies (IgG) served as a negative control for immunocytochemistry when results were compared to anti-β/A4 immunostaining.

Primary antibody supernatants were diluted 1:5 in immunostaining buffer (2% bovine serum albumin, 0.3M NaCl, 0.02M phosphate, pH 7.2, 0.01% Triton X-100). Incubation was overnight at 4° C. The following day cells were washed 3× for 10 minutes with buffer containing 0.3M NaCl and 20 mM Tris, followed by a 2 hour incubation with 5 μg/ml of biotinylated goat anti-mouse IgG (Jackson Immunoresearch) in immunostaining buffer (without detergent). Cells were washed as before. They were then incubated with streptavidin-horseradish-peroxidase conjugate (Sigma) at 0.25 μg/ml in immunostaining buffer (without detergent) for 2 hours and washed as above. The chromogen used was diaminobenzidine (Sigma) 0.5 mg/ml, imidazole (Sigma) 1 mg/ml, in 100 mM Tris, pH 7.0. Hydrogen peroxide was added just before use at 0.015% (1 μl of 30% $H_2O_2$/2 ml). The reaction proceeded for 2 minutes at room temperature followed by two rinses with distilled water. The cells were then post-fixed in 2% glutaraldehyde as for routine electron microscopy except that sections that were photographed were not counterstained with lead or uranium salts.

The mean values corresponding to the frequency of membrane processes at the electron microscopy level was compared using ANOVA followed by the Tukey protected T-test.

PC12 cell lines transfected with β/A4 C-terminal DNA (AC126 and AC127) were observed to be morphologically altered. Compared to untransfected PC12 cells (NN), and cells transfected with vector alone (V120), the β/A4-positive transfectants were noticeable larger (FIG. 6, Panels C and D) and had a tendency to aggregate at high density.

Figure 7:
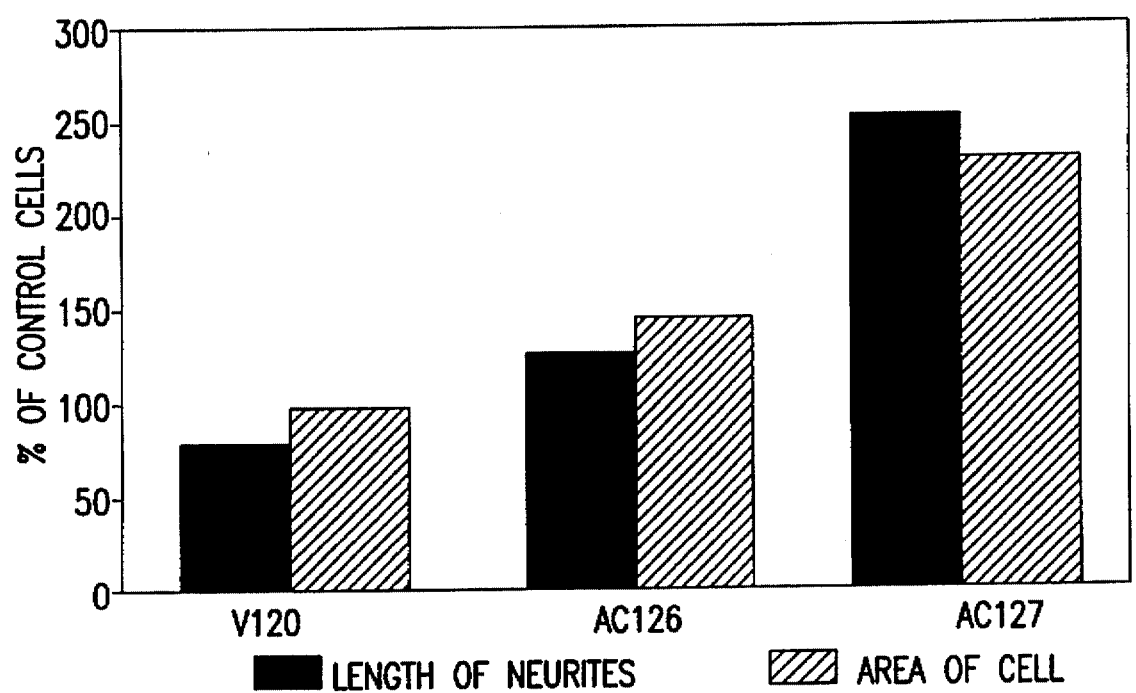
FIG. 7 shows a graphical representation of neurite length and cell size for cells transfected with insertless vector (V120) and β/A4 transfected cells (AC126 and AC127).

Quantitative morphometric light microscopic analyses indicated that the numbers of neurites were not elevated in AC 126 and AC127 cells (75% and 85% of NN). By contrast, neurite length was significantly increased in AC126 and AC127 relative to NN (123% and 254%, resp.) as was cellular area (144% and 234%, respectively) (FIG. 7). V120 failed to exhibit increases in the length of neurites or the area of cells (76% and 96%, respectively, the values of NN cells, FIG. 7).

Figure 8A:
FIG. 8 shows electron micrographs of untransfected (Panel A) and β/A4 transfected (Panel B) PC12 cells.
Figure 8B:
Figure 9A:
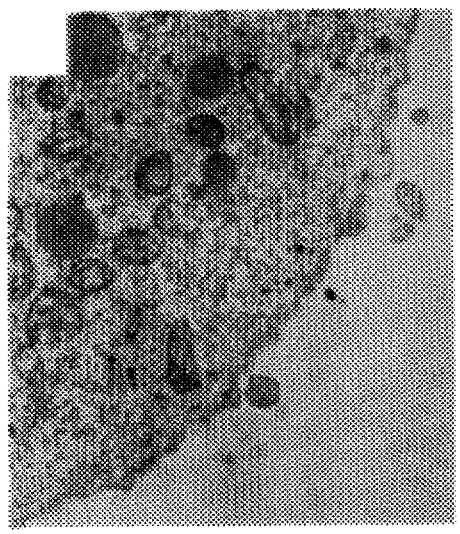
FIG. 9 shows electron micrographs of membrane processes from untransfected cells (Panel A), insertless vector transfected cells (Panel B), and β/A4 transfected AC126 (Panel C) and AC127 (Panel D) cells.
Figure 9B:
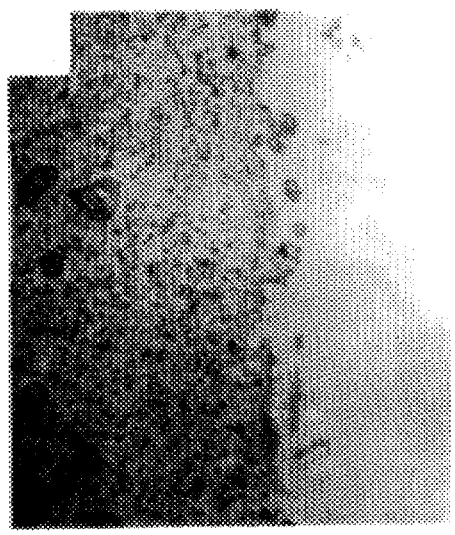
Figure 9C:
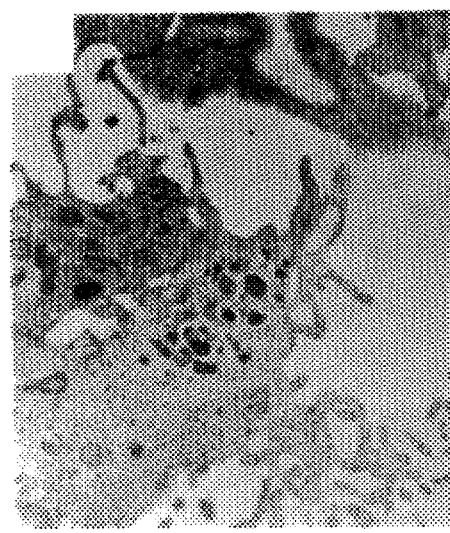
Figure 9D:

By electron microscopy NN and V120 cells were morphologically dissimilar to β/A4-positive transfectants. As anticipated from the light level microscopy AC126 and AC127 cells and nuclei appeared larger than controls and contained more extensive and irregular processes along the entire cell surface. Representative examples are shown in FIG. 8. There was no significant difference among the four cell types (NN, V120, AC126, AC127) with respect to the nuclear to cytoplasmic ratio; the nucleus consisted of approximately 29% of the total volume of the cell.

AC126 and AC127 cell lines appeared to contain fewer chromaffin granules throughout the cytoplasm; however, mitochondrial size and density were unchanged in β/A4-positive transfectants relative to controls. The characteristic shape and well-defined cristae were preserved and no significant differences were observed for the area of the cell occupied by mitochondria. The number of lipofuscin granules was not significantly altered. No differences were observed with respect to ribosomes, polysomes, rough or smooth endoplasmic reticulum, lamellar bodies or Golgi apparatus.

Cell membranes were examined by electron microscopy to assess apparent morphologic modifications in β/A4 amyloid-positive transfectants relative to controls. Detailed scrutiny of AC126 and AC127 cell lines revealed increased numbers of membranous elaborations that resembled microvilli and blebs (FIG. 9).

Figure 10:
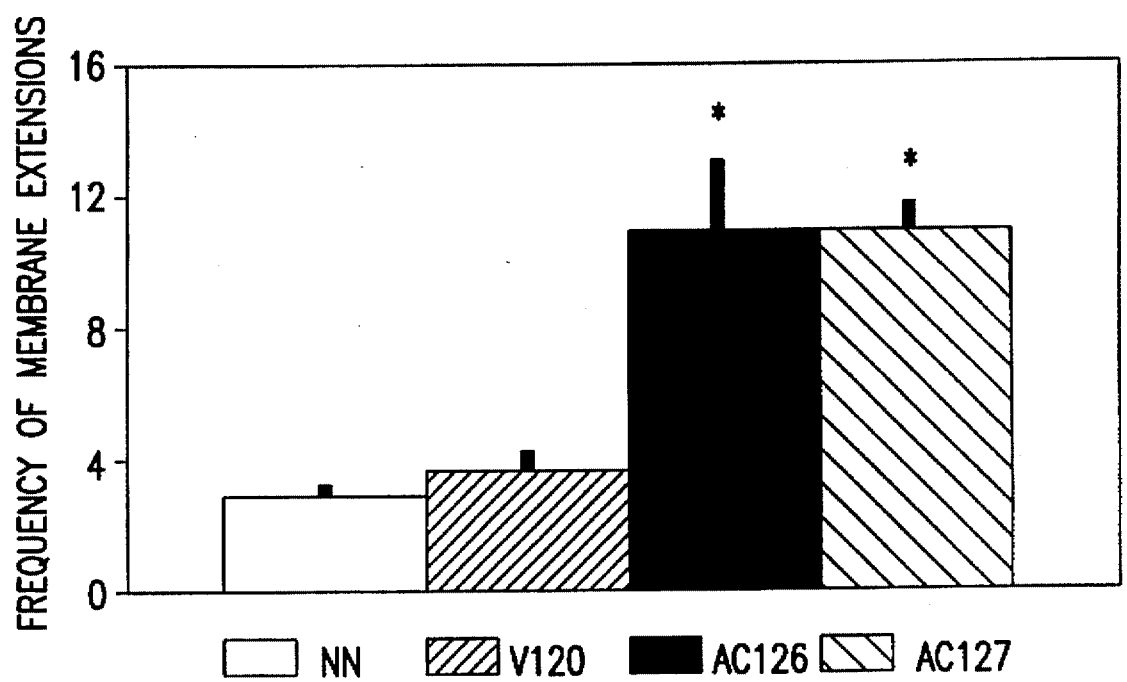
FIG. 10 shows a graphical representation of the frequency of microvilli and/or bleb-like structures in membranes of untransfected (NN), insertless vector transfected (V120) and β/A4 transfected (AC126 and AC127) cells.
Figure 11A:
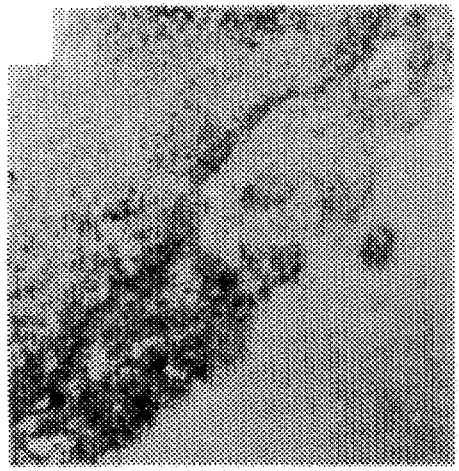
FIG. 11 shows electron micrographs of untransfected cells (Panel A), cells transfected with insertless vector (Panel B), and β/A4 transfected AC126 (Panel C) and AC127 cells (Panel D).
Figure 11B:
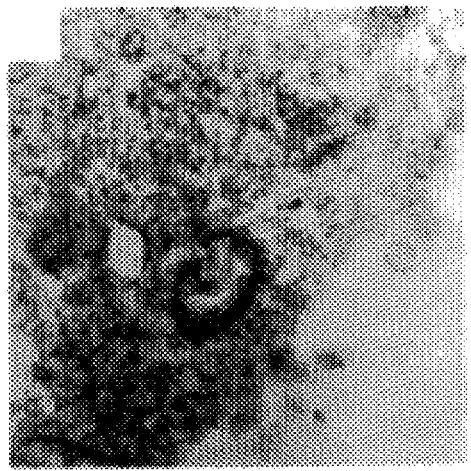
Figure 11C:
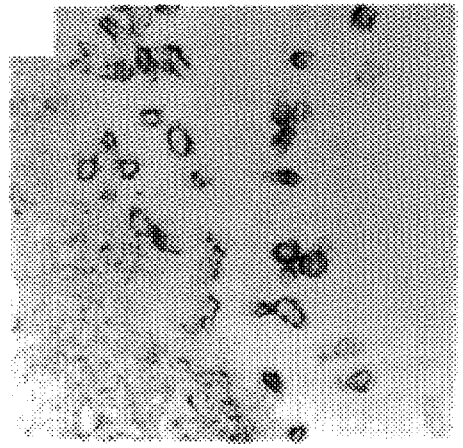
Figure 11D:
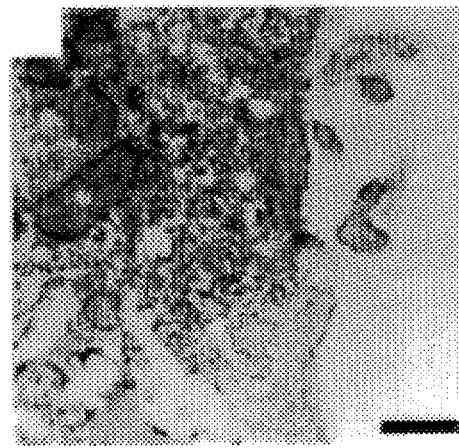

Cell surface elaborations in controls and in β/A4 positive transfectants were quantified and compared. There were significant increases in the frequency of these structures in β/A4-positive transfectants compared to normal control and V120 cells (FIG. 10). There were no significant differences between V120 and NN cells.

The possible relationship between sites of increased β/A4 accumulation and the appearance of membrane extensions at the cell surface was examined by electron microscopy of immunostained sections. After application of monoclonal antibodies prepared against β/A4, electron micrographs of AC126 and AC127 transfectants were contrasted with control cells. The two β/A4-positive cell lines exhibited increased levels of antigen within the cell body and there was prominent immunostaining along the length of the plasma membrane (FIG. 11). Deposits of the β/A4 amyloid antigen were also concentrated within membrane processes resembling blebs and microvilli (FIG. 11).

Figure 12A:
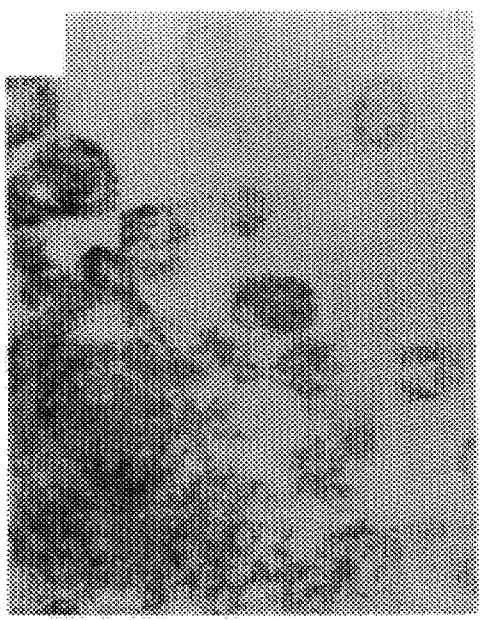
FIG. 12 shows electron micrographs of immunostained cells using anti-ribonuclease inhibitor protein antibody (Panel A) or anti-β/A4 antibody (Panel B).
Figure 12B:
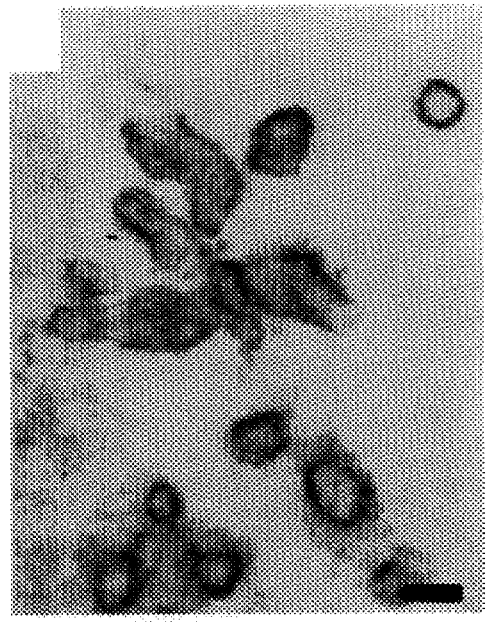

To demonstrate that anti-amyloid mAbs did not label plasma membranes non-specifically, an unrelated control mAb to a cytoplasmic protein was included for comparison. The latter has high affinity for the rat and human ribonuclease inhibitor protein (RIP). Both mAbs were applied to AC126 cells using identical procedures. The anti-RIP mAb lightly labeled cell cytoplasm in a diffuse pattern and failed to detect membranes (FIG. 12A). By contrast, the anti-β/A4 mAb stained membranes of processes, as before (FIG. 12B), indicating that non-specific binding of IgG did not preferentially occur when using the described immunocytochemical methodology.

These results demonstrate that the PC12 cells were substantially altered by expression of the beta amyloid peptide. They suggest that insertion of the β/A4 peptide into the cell membrane allows its expansion and acts in concert with other unidentified factors to allow PC12 cells to enlarge and to form unusually elongated neurites. Finally, they suggest that β/A4 peptide likely contributes to the increased aggregation of the transfected PC12 cells.

The data for cellular area and neurite length of PC12 cells and AC127 cells averaged over a large number of experiments is shown in Table I, below.

TABLE I

| Alteration of PC12 Cell Morphology by Beta/A4 Peptide | | |
|---|---|---|
| | PC12 Cells | AC127 Cells |
| Cellular area (μm$^2$) | 274.76 ± 31 | 642.28 ± 59 |
| % increase | — | 234 |
| Neurite length (μm) | 10.36 ± 1.21 | 26.27 ± 3.32 |
| % increase | — | 254 |

EXAMPLE 3

Reversal of β/A4 Peptide-Induced Morphological Alteration by Oligonucleotides

Two oligonucleotides were tested for their ability to reverse β/A4 peptide-induced morphological alterations in PC12 cells. Both of the oligonucleotides tested were oligonucleoside phosphorothioates (all phosphorothioate internucleoside linkages). The first of these oligonucleotides had the nucleotide sequence [SEQ ID NO. 1] 5'-CCTCTCTGTTTAAAACTTTATCCAT-3'. This sequence is complementary to a nucleic acid sequence that includes the initiation codon from which the β/A4 peptide sequence is translated, in this case encompassing the SV40 T antigen initiation codon. The second oligonucleotide tested had the nucleotide sequence [SEQ ID NO. 2] 5'-TTCATATCCTGAGTCATGTCG-3'. This oligonucleotide is complementary to a portion of the APP coding sequence (encoding amino acids 601–607), which corresponds to the sequence encoding amino acids 5–11 of the β/A4 peptide.

In the experiments that follow, cell size and length of neurites were determined at the light microscope level using an image analysis measurement system containing microdensitometry computer software (obtained from Bioquant, R & M Biometrics, Inc., Nashville, Tenn.). In general, quantitative data on cell parameters (volume, length) for comparison purposes could only be obtained by use of the computer based optical imaging system, rather than by a qualitative comparison of photographs.

Initially, data was collected from normal control PC12 cells and compared to AC127 cells that overexpress beta amyloid in order to establish baseline data. In some experiments, it appeared that the increase in cellular area may have preceded the lengthening of neurites. Morphometric measurements were carried out as described above. The control PC12 cells had a cellular area of $274.76\pm31$ $\mu m^2$ and the neurites had a length of $10.36\pm1.21$ $\mu m$. The AC127 cells had a cellular area of $642.28\pm59$ $\mu m^2$ (234% increase in area) and the neurites had a length of $26.27\pm3.32$ $\mu m$ (254% increase in length). See, Table 1.

Figure 14A:
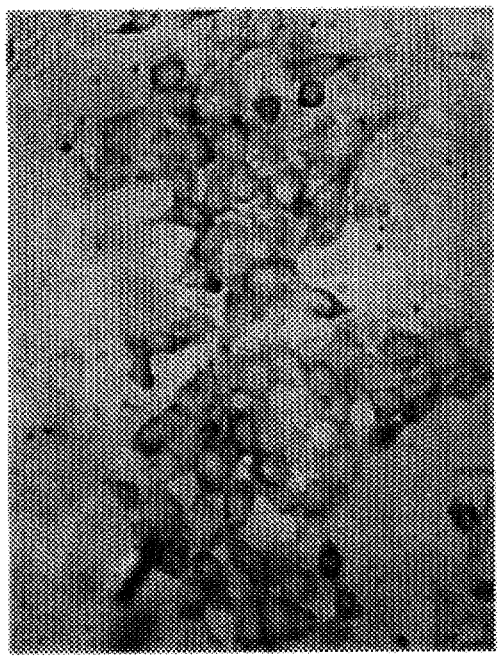
FIGS. 14A and 14B depict immunostained AC127 cells that have been grown in the absence (FIG. 14A) or presence (FIG. 14B) of the antisense oligonucleotide having SEQ ID NO. 1.
Figure 14B:
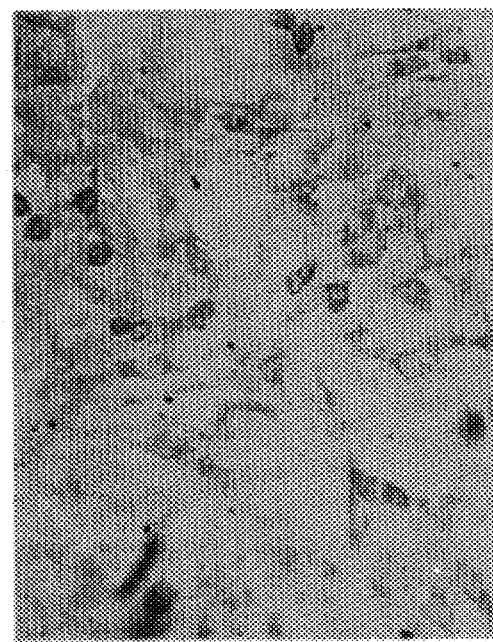

In a first set of experiments, AC127 cells, prepared as described in Example 2, were cultured for 8 days in the presence or absence of 50 µg/ml of one of the two test oligonucleotides. Morphological points were then compared for the oligonucleotide-treated and untreated cells. Treatment of cells with the oligonucleotide that is complementary to the initiation codon from which β/A4 peptide is translated [SEQ ID NO. 1] resulted in greatly diminished immune staining for β/A4 peptide. As shown in FIGS. 14A and 14B, immunostaining was noticeably darker for the amyloid positive cells that did not receive the antisense oligonucleotide (FIG. 14A) compared to cells that received the oligonucleotide (FIG. 14B). In addition, these treated cells were clearly disaggregrated. In an individual experiment, the size of the treated cells diminished from $455.76\pm33.11$ $\mu m^2$ to $299.12\pm31.98$ $\mu m^2$ (average of 50 cells).

In another individual experiment, treatment of cells with the oligonucleotide complementary to the β/A4 peptide coding sequence [SEQ ID NO. 2] resulted in a reduction in cell area from $751.67\pm111.35$ $\mu m^2$ to $286.25\pm60.55$ $\mu m^2$ (average of 25 cells).

In a side-by-side comparison, each oligonucleotide was equally effective in reversing morphological changes induced in PC12 cells by β/A4 peptide, and a combination of the two was similarly effective. Untreated cells had an area of $715.16\pm66.96$ $\mu m^2$. Cells treated with the oligonucleotide having SEQ ID NO. 1 had an area of $378.71\pm36.29\mu^2$. Cells treated with the oligonucleotide having SEQ ID NO. 2 had an area of $347.12\pm35.36$ $\mu m^2$. Fifty cells were measured in each experiment.

In a further experiment, the effects of a mixture of the two antisense oligonucleotides on the cellular area of amyloid-positive PC12 cells were determined. To the cultured cells were added 0 or 50 µg/ml of a mixture of antisense oligonucleotides having SEQ ID NO. 1 and SEQ ID NO. 2. Cells cultured in the absence of the antisense oligonucleotides had an area of $786.69\pm68.23$ $\mu m^2$ compared to $386.55\pm34.08$ $\mu m^2$ for cells treated with the mixture. Fifty cells were measured. Thus, the results show that a mixture of the two antisense oligonucleotides significantly reduced the size of the cells.

Next, the effects of the antisense oligonucleotide having SEQ ID NO. 2 on the length of neurites of amyloid-positive PC12 cells were determined. Cells that overexpress beta amyloid extend neurites to lengths that eventually reach nearly twice that of normal control PC12 cells. In this experiment, the effect of the antisense oligonucleotide having SEQ ID NO. 2 was determined on cells having normal length and cells having abnormally long extensions. Normal control PC12 neurites had a length of $10.36\pm1.21$ $\mu m$. In a first group, the neurite length of amyloid positive cells was $13.12\pm1.21$ $\mu m$ compared to $13.31\pm1.06$ $\mu m$ after treatment with the antisense oligonucleotide. In a second group, the neurite length of amyloid positive cells was $14.29\pm1.23$ $\mu m$ compared to $11.80\pm0.94$ $\mu m$ after treatment with the antisense oligonucleotide. In a third group, the neurite length of amyloid positive cells was $22.66\pm3.45$ $\mu m$ compared to $8.952\pm1.14$ $\mu m$ after treatment with the antisense oligonucleotide. This last group of cells had neurites which were abnormally long. These data demonstrate that the antisense oligonucleotide having SEQ ID NO. 2 is effective in reducing the length of neurites in cells that overexpress beta amyloid only when the transfectants spread extensions to a greater than normal length compared to control values.

In a further experiment, the effectiveness of antisense oligonucleotides having the following sequences and which are completely unrelated to the beta amyloid protein were tested:

[SEQ ID NO. 13] 5'-TTGTTGCGCAGCAGCGTCGTC-3'
[SEQ ID NO. 14] 5'-GGCAAGCTTTATTGAGGCTTAAGCA-3'

An equimolar mixture of the two oligonucleotides were employed at a total concentration of 50 µg/ml. The average size of transfected cells prior to treatment was 560.45 µm compared to 379.29 µm after treatment with the mixture of antisense oligonucleotides having SEQ ID NOS. 13 and 14.

Taken all together, these data show that anti-beta/A4 oligonucleotides effectively reduce the increased size of beta positive cells by approximately 50% The resultant treated cells were, on the average, no more than 18% larger than normal control PC12 cells. By contrast, the oligonucleotides which are unrelated to beta amyloid regulation reduced the size of beta positive PC12 cells by 32% The resultant cells were, on the average, 28% larger than normal control PC12 cells. Thus, antisense oligonucleotides that are complementary to either the initiation codon from which β/A4 peptide is translated or a nucleotide sequence encoding β/A4 peptide are capable of reversing morphological changes that have been wrought upon cells by β/A4 peptide.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An oligonucleotide that is capable of reversing morphological changes induced upon cells by beta/A4 peptide, the oligonucleotide having from about 8 to about 100 nucleotides and being complementary to a nucleotide sequence of an RNA encoding beta/A4 peptide, such sequence comprising the initiation codon for APP, wherein the oligonucleotide has at least one internucleotide linkage selected from the group consisting of phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages.

2. The oligonucleotide according to claim 1, wherein the oligonucleotide is a mixed backbone oligonucleotide comprising a phosphorothioate or phosphorodithioate region and an alkylphosphonate or alkylphosphonothioate region.

3. The oligonucleotide according to claim 1, wherein the oligonucleotide comprises a ribonucleotide region and a deoxyribonucleotide region.

4. The oligonucleotide according to claim 1, wherein the oligonucleotide has a 3' cap structure.

5. The oligonucleotide according to claim 1, wherein the oligonucleotide has a self-complementary region at the 3' end that hybridizes intramolecularly with the oligonucleotide to form an exonuclease resistant hairpin-like structure.

6. An oligonucleotide that is capable of reversing morphological changes induced upon cells by beta/A4 peptide, the oligonucleotide having from about 8 to about 100 nucleotides and being complementary to a nucleotide sequence of an RNA encoding APP, wherein the oligonucleotide has at least one internucleotide linkage selected from the group consisting of phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages.

7. The oligonucleotide according to claim 6, wherein the oligonucleotide is a mixed backbone oligonucleotide comprising a phosphorothioate or phosphorodithioate region and an alkylphosphonate or alkylphosphonothioate region.

8. The oligonucleotide according to claim 6, wherein the oligonucleotide comprises a ribonucleotide region and a deoxyribonucleotide region.

9. The oligonucleotide according to claim 6, wherein the oligonucleotide has a 3' cap structure.

10. The oligonucleotide according to claim 6, wherein the oligonucleotide has a self-complementary region at the 3' end that hybridizes intramolecularly with the oligonucleotide to form an exonuclease resistant hairpin-like structure.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCTCTCTGTT TAAAACTTTA TCCAT 25

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TTCATATCCT GAGTCATGTC G 21

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GTCCCAGCGC TACGACGGGC CAAA 24

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GTCCCAGCGC TAC 13

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TACGACGGGC CAAA 14

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GTCCCAGCGC TACGACGGGC C    21

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GTCCCAGCGC TACGACGG    18

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GTCCCAGCGC TACGA    15

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CCAGCGCTAC GACGGGCCAA A    21

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GCGCTACGAC GGGCCAAA    18

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CTACGACGGG CCAAA    15

( 2 ) INFORMATION FOR SEQ ID NO:12:

( i ) SEQUENCE CHARACTERISTICS:
        ( A ) LENGTH: 3353 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:12:

-continued

| | | | | | |
|---|---|---|---|---|---|
|AGTTTCCTCG|GCAGCGGTAG|GCGAGAGCAC|GCGGAGGAGC|GTGCGCGGGG|CCCCGGGAGA|60|
|CGGCGGCGGT|GGCGGCGCGG|GCAGAGCAAG|GACGCGGCGG|ATCCCACTCG|CACAGCAGCG|120|
|CACTCGGTGC|CCCGCGCAGG|GTCGCGATGC|TGCCCGGTTT|GGCACTGCTC|CTGCTGGCCG|180|
|CCTGGACGGC|TCGGGCGCTG|GAGGTACCCA|CTGATGGTAA|TGCTGGCCTG|CTGGCTGAAC|240|
|CCCAGATTGC|CATGTTCTGT|GGCAGACTGA|ACATGCACAT|GAATGTCCAG|AATGGGAAGT|300|
|GGGATTCAGA|TCCATCAGGG|ACCAAAACCT|GCATTGATAC|CAAGGAAGGC|ATCCTGCAGT|360|
|ATTGCCAAGA|AGTCTACCCT|GAACTGCAGA|TCACCAATGT|GGTAGAAGCC|AACCAACCAG|420|
|TGACCATCCA|GAACTGGTGC|AAGCGGGGCC|GCAAGCAGTG|CAAGACCCAT|CCCCACTTTG|480|
|TGATTCCCTA|CCGCTGCTTA|GTTGGTGAGT|TTGTAAGTGA|TGCCCTTCTC|GTTCCTGACA|540|
|AGTGCAAATT|CTTACACCAG|GAGAGGATGG|ATGTTTGCGA|AACTCATCTT|CACTGGCACA|600|
|CCGTCGCCAA|AGAGACATGC|AGTGAGAAGA|GTACCAACTT|GCATGACTAC|GGCATGTTGC|660|
|TGCCCTGCGG|AATTGACAAG|TTCCGAGGGG|TAGAGTTTGT|GTGTTGCCCA|CTGGCTGAAG|720|
|AAAGTGACAA|TGTGGATTCT|GCTGATGCGG|AGGAGGATGA|CTCGGATGTC|TGGTGGGGCG|780|
|GAGCAGACAC|AGACTATGCA|GATGGGAGTG|AAGACAAAGT|AGTAGAAGTA|GCAGAGGAGG|840|
|AAGAAGTGGC|TGAGGTGGAA|GAAGAAGAAG|CCGATGATGA|CGAGGACGAT|GAGGATGGTG|900|
|ATGAGGTAGA|GGAAGAGGCT|GAGGAACCCT|ACGAAGAAGC|CACAGAGAGA|ACCACCAGCA|960|
|TTGCCACCAC|CACCACCACC|ACCACAGAGT|CTGTGGAAGA|GGTGGTTCGA|GTTCCTACAA|1020|
|CAGCAGCCAG|TACCCCTGAT|GCCGTTGACA|AGTATCTCGA|GACACCTGGG|GATGAGAATG|1080|
|AACATGCCCA|TTTCCAGAAA|GCCAAGGAGA|GGCTTGAGGC|CAAGCACCGA|GAGAGAATGT|1140|
|CCCAGGTCAT|GAGAGAATGG|GAAGAGGCAG|AACGTCAAGC|AAAGAACTTG|CCTAAAGCTG|1200|
|ATAAGAAGGC|AGTTATCCAG|CATTTCCAGG|AGAAAGTGGA|ATCTTTGGAA|CAGGAAGCAG|1260|
|CCAACGAGAG|ACAGCAGCTG|GTGGAGACAC|ACATGGCCAG|AGTGGAAGCC|ATGCTCAATG|1320|
|ACCGCCGCCG|CCTGGCCCTG|GAGAACTACA|TCACCGCTCT|GCAGGCTGTT|CCTCCTCGGC|1380|
|CTCGTCACGT|GTTCAATATG|CTAAAGAAGT|ATGTCCGCGC|AGAACAGAAG|GACAGACAGC|1440|
|ACACCCTAAA|GCATTTCGAG|CATGTGCGCA|TGGTGGATCC|CAAGAAAGCC|GCTCAGATCC|1500|
|GGTCCCAGGT|TATGACACAC|CTCCGTGTGA|TTTATGAGCG|CATGAATCAG|TCTCTCTCCC|1560|
|TGCTCTACAA|CGTGCCTGCA|GTGGCCGAGG|AGATTCAGGA|TGAAGTTGAT|GAGCTGCTTC|1620|
|AGAAAGAGCA|AAACTATTCA|GATGACGTCT|TGGCCAACAT|GATTAGTGAA|CCAAGGATCA|1680|
|GTTACGGAAA|CGATGCTCTC|ATGCCATCTT|TGACCGAAAC|GAAAACCACC|GTGGAGCTCC|1740|
|TTCCCGTGAA|TGGAGAGTTC|AGCCTGGACG|ATCTCCAGCC|GTGGCATTCT|TTTGGGGCTG|1800|
|ACTCTGTGCC|AGCCAACACA|GAAAACGAAG|TTGAGCCTGT|TGATGCCCGC|CCTGCTGCCG|1860|
|ACCGAGGACT|GACCACTCGA|CCAGGTTCTG|GGTTGACAAA|TATCAAGACG|GAGGAGATCT|1920|
|CTGAAGTGAA|GATGGATGCA|GAATTCCGAC|ATGACTCAGG|ATATGAAGTT|CATCATCAAA|1980|
|AATTGGTGTT|CTTTGCAGAA|GATGTGGGTT|CAAACAAAGG|TGCAATCATT|GGACTCATGG|2040|
|TGGGCGGTGT|TGTCATAGCG|ACAGTGATCG|TCATCACCTT|GGTGATGCTG|AAGAAGAAAC|2100|
|AGTACACATC|CATTCATCAT|GGTGTGGTGG|AGGTTGACGC|CGCTGTCACC|CCAGAGGAGC|2160|
|GCCACCTGTC|CAAGATGCAG|CAGAACGGCT|ACGAAAATCC|AACCTACAAG|TTCTTTGAGC|2220|
|AGATGCAGAA|CTAGACCCCC|GCCACAGCAG|CCTCTGAAGT|TGGACAGCAA|AACCATTGCT|2280|
|TCACTACCCA|TCGGTGTCCA|TTTATAGAAT|AATGTGGGAA|GAAACAAACC|CGTTTATGA|2340|
|TTTACTCATT|ATCGCCTTTT|GACAGCTGTG|CTGTAACACA|AGTAGATGCC|TGAACTTGAA|2400|

| | | | | | | |
|---|---|---|---|---|---|---|
| TTAATCCACA | CATCAGTAAT | GTATTCTATC | TCTCTTTACA | TTTTGGTCTC | TATACTACAT | 2460 |
| TATTAATGGG | TTTTGTGTAC | TGTAAAGAAT | TTAGCTGTAT | CAAACTAGTG | CATGAATAGA | 2520 |
| TTCTCTCCTG | ATTATTTATC | ACATAGCCCC | TTAGCCAGTT | GTATATTATT | CTTGTGGTTT | 2580 |
| GTGACCCAAT | TAAGTCCTAC | TTTACATATG | CTTTAAGAAT | CGATGGGGGA | TGCTTCATGT | 2640 |
| GAACGTGGGA | GTTCAGCTGC | TTCTCTTGCC | TAAGTATTCC | TTTCCTGATC | ACTATGCATT | 2700 |
| TTAAAGTTAA | ACATTTTTAA | GTATTTCAGA | TGCTTTAGAG | AGATTTTTTT | TCCATGACTG | 2760 |
| CATTTTACTG | TACAGATTGC | TGCTTCTGCT | ATATTTGTGA | TATAGGAATT | AAGAGGATAC | 2820 |
| ACACGTTTGT | TTCTTCGTGC | CTGTTTTATG | TGCACACATT | AGGCATTGAG | ACTTCAAGCT | 2880 |
| TTTCTTTTTT | TGTCCACGTA | TCTTTGGGTC | TTTGATAAAG | AAAAGAATCC | CTGTTCATTG | 2940 |
| TAAGCACTTT | TACGGGGCGG | GTGGGGAGGG | GTGCTCTGCT | GGTCTTCAAT | TACCAAGAAT | 3000 |
| TCTCCAAAAC | AATTTTCTGC | AGGATGATTG | TACAGAATCA | TTGCTTATGA | CATGATCGCT | 3060 |
| TTCTACACTG | TATTACATAA | ATAAATTAAA | TAAATAACC | CCGGGCAAGA | CTTTTCTTTG | 3120 |
| AAGGATGACT | ACAGACATTA | AATAATCGAA | GTAATTTTGG | GTGGGGAGAA | GAGGCAGATT | 3180 |
| CAATTTTCTT | TAACCAGTCT | GAAGTTTCAT | TTATGATACA | AAAGAAGATG | AAAATGGAAG | 3240 |
| TGGCAATATA | AGGGGATGAG | GAAGGCATGC | CTGGACAAAC | CCTTCTTTTA | AGATGTGTCT | 3300 |
| TCAATTTGTA | TAAAATGGTG | TTTTCATGTA | AATAAATACA | TTCTTGGAGG | AGC | 3353 |

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

TTGTTGCGCA GCAGCGTCGT C           21

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GGCAAGCTTT ATTGAGGCTT AAGCA        25